US010628714B2

(12) United States Patent
Pradeep et al.

(10) Patent No.: US 10,628,714 B2
(45) Date of Patent: Apr. 21, 2020

(54) ENTITY-TRACKING COMPUTING SYSTEM

(71) Applicant: Microsoft Technology Licensing, LLC, Redmond, WA (US)

(72) Inventors: Vivek Pradeep, Redmond, WA (US); Pablo Luis Sala, Bothell, WA (US); John Guido Atkins Weiss, Lake Forest Park, WA (US); Moshe Randall Lutz, Bellevue, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 161 days.

(21) Appl. No.: 15/682,407

(22) Filed: Aug. 21, 2017

(65) Prior Publication Data
US 2018/0231653 A1  Aug. 16, 2018

Related U.S. Application Data

(60) Provisional application No. 62/482,165, filed on Apr. 5, 2017, provisional application No. 62/459,020, filed on Feb. 14, 2017.

(51) Int. Cl.
*G01C 21/12* (2006.01)
*G06K 9/72* (2006.01)
(Continued)

(52) U.S. Cl.
CPC ............ *G06K 9/726* (2013.01); *A61B 5/0205* (2013.01); *A61B 5/0507* (2013.01); *A61B 5/117* (2013.01);
(Continued)

(58) Field of Classification Search
CPC .. G06T 7/74; G06T 7/60; G06T 7/248; G06T 7/70; G06T 2207/10016;
(Continued)

(56) References Cited

U.S. PATENT DOCUMENTS 6,067,673 A   5/2000 Paese et al.
6,119,088 A   9/2000 Ciluffo
(Continued)

FOREIGN PATENT DOCUMENTS

EP   2947476 A1   11/2015
GB   2522922 A    8/2015
(Continued)

OTHER PUBLICATIONS

Cho, et al., "A Multi-Sensor Fusion System for Moving Object Detection and Tracking in Urban Driving Environments" 2014 IEEE International Conference on Robotics & Automation (ICRA), Hong Kong Convention and Exhibition Center May 31-Jun. 7, 2014. 8 pages.
(Continued)

*Primary Examiner* — Shardul D Patel
(74) *Attorney, Agent, or Firm* — Alleman Hall Creasman & Tuttle LLP

(57) ABSTRACT

An entity-tracking computing system receives sensor information from a plurality of different sensors. The positions of entities detected by the various sensors are resolved to an environment-relative coordinate system so that entities identified by one sensor can be tracked across the fields of detection of other sensors.

19 Claims, 18 Drawing Sheets

(51) Int. Cl.

| | | |
|---|---|---|
| *G06K 9/00* | (2006.01) | |
| *G06T 7/70* | (2017.01) | |
| *G06K 9/62* | (2006.01) | |
| *G06F 3/16* | (2006.01) | |
| *G10L 15/18* | (2013.01) | |
| *G06N 20/00* | (2019.01) | |
| *G06T 7/292* | (2017.01) | |
| *H04W 4/33* | (2018.01) | |
| *H04W 4/029* | (2018.01) | |
| *A61B 5/11* | (2006.01) | |
| *A61B 5/117* | (2016.01) | |
| *A61B 5/00* | (2006.01) | |
| *G01S 5/28* | (2006.01) | |
| *G06F 1/3206* | (2019.01) | |
| *G06F 1/3231* | (2019.01) | |
| *G06F 1/324* | (2019.01) | |
| *G06F 3/01* | (2006.01) | |
| *G06F 3/03* | (2006.01) | |
| *G06F 17/27* | (2006.01) | |
| *G06F 21/32* | (2013.01) | |
| *G10L 17/04* | (2013.01) | |
| *G10L 17/08* | (2013.01) | |
| *H04L 12/58* | (2006.01) | |
| *H04L 29/08* | (2006.01) | |
| *H04N 5/232* | (2006.01) | |
| *H04N 7/18* | (2006.01) | |
| *H04N 21/422* | (2011.01) | |
| *H04N 21/442* | (2011.01) | |
| *G06T 7/73* | (2017.01) | |
| *G06T 7/246* | (2017.01) | |
| *G01S 5/18* | (2006.01) | |
| *G06T 7/60* | (2017.01) | |
| *G10L 15/22* | (2006.01) | |
| *G10L 15/28* | (2013.01) | |
| *H04R 1/40* | (2006.01) | |
| *H04R 3/00* | (2006.01) | |
| *H04N 5/33* | (2006.01) | |
| *G10L 15/02* | (2006.01) | |
| *G06N 5/02* | (2006.01) | |
| *G06N 5/04* | (2006.01) | |
| *G10L 15/06* | (2013.01) | |
| *G10L 15/24* | (2013.01) | |
| *G10L 15/26* | (2006.01) | |
| *G10L 15/19* | (2013.01) | |
| *G10L 15/08* | (2006.01) | |
| *G10L 15/32* | (2013.01) | |
| *G10L 25/51* | (2013.01) | |
| *H04L 29/06* | (2006.01) | |
| *A61B 5/0205* | (2006.01) | |
| *A61B 5/05* | (2006.01) | |
| *G01S 13/72* | (2006.01) | |
| *G06F 21/35* | (2013.01) | |
| *G07C 9/00* | (2020.01) | |
| *G08B 13/14* | (2006.01) | |
| *G06F 3/0482* | (2013.01) | |
| *G06F 3/0484* | (2013.01) | |
| *H04N 21/231* | (2011.01) | |
| *G06F 3/0488* | (2013.01) | |
| *G06F 16/70* | (2019.01) | |
| *G01S 5/16* | (2006.01) | |
| *G01S 11/14* | (2006.01) | |
| *G01S 13/86* | (2006.01) | |
| *G06N 3/04* | (2006.01) | |
| *G08B 29/18* | (2006.01) | |
| *G10L 17/00* | (2013.01) | |
| *H04N 5/247* | (2006.01) | |
| *G01S 13/38* | (2006.01) | |
| *G01S 13/88* | (2006.01) | |

(52) U.S. Cl.
CPC .......... *A61B 5/1113* (2013.01); *A61B 5/7475* (2013.01); *G01S 5/18* (2013.01); *G01S 5/28* (2013.01); *G01S 13/726* (2013.01); *G06F 1/324* (2013.01); *G06F 1/3206* (2013.01); *G06F 1/3231* (2013.01); *G06F 3/011* (2013.01); *G06F 3/017* (2013.01); *G06F 3/0304* (2013.01); *G06F 3/0482* (2013.01); *G06F 3/04842* (2013.01); *G06F 3/167* (2013.01); *G06F 17/271* (2013.01); *G06F 17/279* (2013.01); *G06F 21/32* (2013.01); *G06F 21/35* (2013.01); *G06K 9/00214* (2013.01); *G06K 9/00255* (2013.01); *G06K 9/00261* (2013.01); *G06K 9/00288* (2013.01); *G06K 9/00295* (2013.01); *G06K 9/00342* (2013.01); *G06K 9/00362* (2013.01); *G06K 9/00711* (2013.01); *G06K 9/00771* (2013.01); *G06K 9/00973* (2013.01); *G06K 9/6254* (2013.01); *G06K 9/6255* (2013.01); *G06K 9/6289* (2013.01); *G06K 9/6296* (2013.01); *G06N 5/025* (2013.01); *G06N 5/047* (2013.01); *G06N 20/00* (2019.01); *G06T 7/248* (2017.01); *G06T 7/292* (2017.01); *G06T 7/60* (2013.01); *G06T 7/70* (2017.01); *G06T 7/74* (2017.01); *G07C 9/00111* (2013.01); *G08B 13/1427* (2013.01); *G10L 15/02* (2013.01); *G10L 15/063* (2013.01); *G10L 15/08* (2013.01); *G10L 15/18* (2013.01); *G10L 15/1815* (2013.01); *G10L 15/1822* (2013.01); *G10L 15/19* (2013.01); *G10L 15/22* (2013.01); *G10L 15/24* (2013.01); *G10L 15/26* (2013.01); *G10L 15/28* (2013.01); *G10L 15/32* (2013.01); *G10L 17/04* (2013.01); *G10L 17/08* (2013.01); *G10L 25/51* (2013.01); *H04L 51/02* (2013.01); *H04L 63/102* (2013.01); *H04L 67/12* (2013.01); *H04L 67/22* (2013.01); *H04N 5/23219* (2013.01); *H04N 5/332* (2013.01); *H04N 7/181* (2013.01); *H04N 7/188* (2013.01); *H04N 21/231* (2013.01); *H04N 21/42203* (2013.01); *H04N 21/44218* (2013.01); *H04N 21/44222* (2013.01); *H04R 1/406* (2013.01); *H04R 3/005* (2013.01); *H04W 4/029* (2018.02); *H04W 4/33* (2018.02); *A61B 5/05* (2013.01); *A61B 5/1118* (2013.01); *G01S 5/16* (2013.01); *G01S 11/14* (2013.01); *G01S 13/38* (2013.01); *G01S 13/867* (2013.01); *G01S 13/888* (2013.01); *G06F 3/0488* (2013.01); *G06F 16/70* (2019.01); *G06F 2203/0381* (2013.01); *G06F 2221/2111* (2013.01); *G06K 2209/09* (2013.01); *G06N 3/0445* (2013.01); *G06T 2207/10016* (2013.01); *G06T 2207/10024* (2013.01); *G06T 2207/20101* (2013.01); *G06T 2207/30196* (2013.01); *G06T 2207/30201* (2013.01); *G06T 2207/30204* (2013.01); *G06T 2207/30232* (2013.01); *G07C 9/00134* (2013.01); *G08B 29/186* (2013.01); *G10L 17/00* (2013.01); *G10L 2015/0635* (2013.01); *G10L 2015/088* (2013.01); *G10L 2015/223* (2013.01); *G10L 2015/225* (2013.01); *G10L*

*2015/228* (2013.01); *H04N 5/247* (2013.01); *Y02D 10/126* (2018.01); *Y02D 10/173* (2018.01)

(58) Field of Classification Search
CPC . G06T 2207/10024; G06T 2207/30232; G06T 2207/30201; G06T 2207/30196; G06T 2207/30204; G06T 2207/20101; G10L 15/26; G10L 15/28; G10L 15/22; G10L 15/1815; G10L 17/00; G10L 15/18; G10L 15/063; G10L 2015/228; G10L 2015/0635; G10L 2015/223; G10L 2015/088; G10L 2015/225; G10L 15/24; H04N 21/231; H04N 5/247; H04N 5/332; G06K 9/00711; G06K 9/6255; G06K 9/6296; G06K 9/00288; G06K 9/00255; G06K 9/00342; G06K 9/00214; G06K 9/6289; G06K 9/6254; G06K 2209/09; G06K 9/00295; G06F 3/04842; G06F 3/0482; G06F 21/35; G06F 17/271; G06F 3/167; G06F 16/70; G06F 2203/0381; G06F 17/30781; G06F 3/0488; G06F 3/017; G08B 13/1427; A61B 5/0507; H04L 63/102; G06N 5/047; G06N 5/025; G06N 3/0445; H04R 1/406; H04R 3/005; G01S 5/18; G01S 13/867; G01S 11/14; G01S 5/16; G01S 13/38; G01S 13/888; G01S 13/726; Y02D 10/126; Y02D 10/173; G07C 9/00134; G07C 9/00111
USPC .......... 701/495; 250/340, 394, 362; 700/115
See application file for complete search history.

(56) References Cited

U.S. PATENT DOCUMENTS

| | | | |
|---|---|---|---|
| 6,332,122 B1 | 12/2001 | Ortega et al. | |
| 6,442,524 B1 | 8/2002 | Ecker et al. | |
| 6,477,500 B2 | 11/2002 | Maes | |
| 6,496,799 B1 | 12/2002 | Pickering | |
| 6,574,601 B1 | 6/2003 | Brown et al. | |
| 6,727,925 B1 | 4/2004 | Bourdelais | |
| 6,728,679 B1 | 4/2004 | Strubbe et al. | |
| 6,816,730 B2 | 11/2004 | Davies et al. | |
| 6,873,953 B1 | 3/2005 | Lennig | |
| 7,019,749 B2 | 3/2006 | Guo et al. | |
| 7,050,110 B1 | 5/2006 | Lienhart et al. | |
| 7,330,566 B2 | 2/2008 | Cutler | |
| 7,475,010 B2 | 1/2009 | Chao | |
| 7,610,365 B1 | 10/2009 | Kraft et al. | |
| 7,716,056 B2 | 5/2010 | Weng et al. | |
| 7,803,050 B2 | 9/2010 | Mao et al. | |
| 8,139,945 B1 | 3/2012 | Amir et al. | |
| 8,165,087 B2 | 4/2012 | Panabaker | |
| 8,170,875 B2 | 5/2012 | Hetherington et al. | |
| 8,213,689 B2 | 7/2012 | Yagnik et al. | |
| 8,265,252 B2 | 9/2012 | Ducheneaut et al. | |
| 8,326,627 B2 | 12/2012 | Kennewick et al. | |
| 8,340,975 B1 | 12/2012 | Rosenberger | |
| 8,374,879 B2 | 2/2013 | Falcon et al. | |
| 8,453,402 B2 | 6/2013 | Huang | |
| 8,457,959 B2 | 6/2013 | Kaiser | |
| 8,543,402 B1 | 9/2013 | Ma | |
| 8,639,762 B2 | 1/2014 | Rasmussen et al. | |
| 8,644,842 B2 | 2/2014 | Arrasvuori et al. | |
| 8,712,758 B2 | 4/2014 | Crouch et al. | |
| 8,752,145 B1 | 6/2014 | Dotan et al. | |
| 8,762,150 B2 | 6/2014 | Edgington et al. | |
| 8,762,156 B2 | 6/2014 | Chen | |
| 8,779,965 B2 | 7/2014 | Sentelle et al. | |
| 8,805,691 B2 | 8/2014 | Genly | |
| 8,861,924 B2 | 10/2014 | Meads et al. | |
| 8,862,156 B2 | 10/2014 | Bell et al. | |
| 8,903,128 B2 | 12/2014 | Shet et al. | |
| 8,913,103 B1 | 12/2014 | Sargin et al. | |
| 8,942,986 B2 | 1/2015 | Cheyer et al. | |
| 8,949,359 B2 | 2/2015 | Rasmussen et al. | |
| 9,037,601 B2 | 5/2015 | Palay | |
| 9,070,366 B1 | 6/2015 | Mathias et al. | |
| 9,085,303 B2 | 7/2015 | Wolverton et al. | |
| 9,119,512 B2 | 9/2015 | Martins, Jr. et al. | |
| 9,123,330 B1 | 9/2015 | Sharifi et al. | |
| 9,171,542 B2 | 10/2015 | Gandrabur et al. | |
| 9,230,544 B2 | 1/2016 | Kwon et al. | |
| 9,268,406 B2 | 2/2016 | Geisner et al. | |
| 9,300,925 B1 | 3/2016 | Zhang | |
| 9,307,355 B2 | 4/2016 | Nehrenz et al. | |
| 9,311,932 B2 | 4/2016 | Carter | |
| 9,318,105 B1 | 4/2016 | Khosla | |
| 9,348,990 B2 | 5/2016 | Chuaprasert et al. | |
| 9,368,114 B2 | 6/2016 | Larson et al. | |
| 9,378,740 B1 | 6/2016 | Rosen et al. | |
| 9,380,177 B1 | 6/2016 | Rao et al. | |
| 9,389,681 B2 | 7/2016 | Sankar et al. | |
| 9,412,392 B2 | 8/2016 | Lindahl | |
| 9,424,840 B1 | 8/2016 | Hart et al. | |
| 9,495,331 B2 | 11/2016 | Govrin et al. | |
| 9,495,613 B2 | 11/2016 | Holz et al. | |
| 9,507,977 B1 | 11/2016 | Mor et al. | |
| 9,508,341 B1 | 11/2016 | Parlikar et al. | |
| 9,514,227 B1 | 12/2016 | Garrett et al. | |
| 9,558,749 B1 | 1/2017 | Secker-Walker et al. | |
| 9,576,574 B2 | 2/2017 | van Os | |
| 9,622,059 B2 | 4/2017 | Bouzid et al. | |
| 9,626,352 B2 | 4/2017 | Allen et al. | |
| 9,633,652 B2 | 4/2017 | Kumiawati et al. | |
| 9,761,055 B2 | 9/2017 | Miller | |
| 9,767,616 B2 | 9/2017 | Miller | |
| 9,842,299 B2 | 12/2017 | Stolarz et al. | |
| 10,178,301 B1 | 1/2019 | Welbourne et al. | |
| 10,276,149 B1 | 4/2019 | Liang et al. | |
| 2003/0103647 A1 | 6/2003 | Rui et al. | |
| 2003/0131064 A1 | 7/2003 | Bell et al. | |
| 2005/0182627 A1 | 8/2005 | Tanaka et al. | |
| 2005/0216264 A1 | 9/2005 | Attwater et al. | |
| 2005/0225427 A1* | 10/2005 | Bell | G06F 21/35 340/5.2 |
| 2005/0285774 A1 | 12/2005 | Wittenberg et al. | |
| 2006/0028552 A1* | 2/2006 | Aggarwal | G01S 3/7864 348/169 |
| 2007/0024487 A1* | 2/2007 | Zemany | G01S 13/38 342/22 |
| 2007/0100480 A1 | 5/2007 | Sinclair et al. | |
| 2007/0152157 A1* | 7/2007 | Page | G06K 9/3216 250/340 |
| 2007/0198245 A1 | 8/2007 | Kamatani et al. | |
| 2007/0271086 A1 | 11/2007 | Peters et al. | |
| 2008/0030345 A1* | 2/2008 | Austin | A61B 90/90 340/572.8 |
| 2008/0071547 A1 | 3/2008 | Prieto et al. | |
| 2008/0077015 A1 | 3/2008 | Boric-Lubecke et al. | |
| 2008/0288251 A1 | 11/2008 | Cooper et al. | |
| 2009/0066690 A1 | 3/2009 | Harrison | |
| 2009/0303342 A1 | 12/2009 | Corcoran et al. | |
| 2009/0319269 A1 | 12/2009 | Aronowitz | |
| 2010/0073363 A1 | 3/2010 | Densham et al. | |
| 2010/0100851 A1 | 4/2010 | Clark et al. | |
| 2010/0195906 A1 | 8/2010 | Uliyar et al. | |
| 2011/0184735 A1 | 7/2011 | Flaks et al. | |
| 2011/0216090 A1 | 9/2011 | Woo et al. | |
| 2011/0219339 A1 | 9/2011 | Densham | |
| 2011/0298967 A1 | 12/2011 | Clavin et al. | |
| 2012/0026335 A1* | 2/2012 | Brown | G01S 5/16 348/159 |
| 2012/0253791 A1 | 10/2012 | Heck et al. | |
| 2012/0265535 A1 | 10/2012 | Bryant-rich et al. | |
| 2012/0268604 A1 | 10/2012 | Tree | |
| 2013/0110519 A1 | 5/2013 | Cheyer et al. | |
| 2013/0117377 A1 | 5/2013 | Miller | |
| 2013/0212501 A1 | 8/2013 | Anderson et al. | |
| 2013/0253936 A1 | 9/2013 | Harvey | |
| 2013/0342568 A1 | 12/2013 | Ambrus et al. | |

(56) References Cited

U.S. PATENT DOCUMENTS

| | | | |
|---|---|---|---|
| 2014/0033071 A1* | 1/2014 | Gruber | G06Q 10/1097 |
| | | | 715/752 |
| 2014/0067679 A1 | 3/2014 | O'Reilly et al. | |
| 2014/0156276 A1 | 6/2014 | Nakano et al. | |
| 2014/0180629 A1 | 6/2014 | Dokmanic et al. | |
| 2014/0214421 A1 | 7/2014 | Shriberg et al. | |
| 2014/0214429 A1 | 7/2014 | Pantel | |
| 2014/0222422 A1 | 8/2014 | Sarikaya et al. | |
| 2014/0244263 A1 | 8/2014 | Pontual et al. | |
| 2014/0272821 A1 | 9/2014 | Pitschel et al. | |
| 2014/0330569 A1 | 11/2014 | Kolavennu et al. | |
| 2014/0341440 A1 | 11/2014 | Walch | |
| 2014/0365226 A1 | 12/2014 | Sinha | |
| 2015/0016642 A1 | 1/2015 | Walsh et al. | |
| 2015/0019714 A1 | 1/2015 | Shaashua et al. | |
| 2015/0025887 A1 | 1/2015 | Sidi et al. | |
| 2015/0032456 A1* | 1/2015 | Wait | G10L 15/26 |
| | | | 704/275 |
| 2015/0035976 A1 | 2/2015 | Mayuzumi | |
| 2015/0102996 A1 | 4/2015 | Yim et al. | |
| 2015/0138332 A1* | 5/2015 | Cheng | G06K 9/00771 |
| | | | 348/77 |
| 2015/0149179 A1 | 5/2015 | Korbecki | |
| 2015/0149182 A1 | 5/2015 | Kalns et al. | |
| 2015/0162000 A1 | 6/2015 | Di censo et al. | |
| 2015/0172285 A1 | 6/2015 | Lo et al. | |
| 2015/0249664 A1 | 9/2015 | Talhami et al. | |
| 2015/0340033 A1 | 11/2015 | Di fabbrizio et al. | |
| 2015/0347114 A1 | 12/2015 | Yoon | |
| 2016/0063989 A1 | 3/2016 | Deleeuw | |
| 2016/0086018 A1 | 3/2016 | Lemoff | |
| 2016/0088043 A1 | 3/2016 | Jiang et al. | |
| 2016/0092732 A1 | 3/2016 | Black | |
| 2016/0138247 A1* | 5/2016 | Conway | G01S 7/22 |
| | | | 701/50 |
| 2016/0148417 A1 | 5/2016 | Kim et al. | |
| 2016/0155443 A1 | 6/2016 | Khan et al. | |
| 2016/0173293 A1 | 6/2016 | Kennedy | |
| 2016/0179831 A1* | 6/2016 | Gruber | G10L 15/26 |
| | | | 704/235 |
| 2016/0187961 A1 | 6/2016 | Elibol et al. | |
| 2016/0203002 A1 | 7/2016 | Kannan et al. | |
| 2016/0210411 A1* | 7/2016 | Mentis | G06F 19/321 |
| 2016/0225373 A1* | 8/2016 | Casado | G10L 15/222 |
| 2016/0234616 A1 | 8/2016 | Gateau | |
| 2016/0283185 A1 | 9/2016 | Mclaren et al. | |
| 2016/0342702 A1 | 11/2016 | Barve et al. | |
| 2016/0358598 A1 | 12/2016 | Williams et al. | |
| 2016/0360336 A1 | 12/2016 | Gross et al. | |
| 2016/0380929 A1 | 12/2016 | Katis et al. | |
| 2017/0013409 A1 | 1/2017 | Cerchio et al. | |
| 2017/0025124 A1 | 1/2017 | Mixter et al. | |
| 2017/0032021 A1 | 2/2017 | Watanachote | |
| 2017/0032787 A1 | 2/2017 | Dayal | |
| 2017/0039423 A1 | 2/2017 | Cork et al. | |
| 2017/0039602 A1 | 2/2017 | Shi-nash et al. | |
| 2017/0068423 A1 | 3/2017 | Napolitano et al. | |
| 2017/0078573 A1* | 3/2017 | Chen | H04N 5/23241 |
| 2017/0169476 A1 | 6/2017 | Nomula et al. | |
| 2017/0185375 A1 | 6/2017 | Martel et al. | |
| 2017/0230705 A1 | 8/2017 | Pardue et al. | |
| 2017/0249309 A1 | 8/2017 | Sarikaya | |
| 2017/0278480 A1 | 9/2017 | Sung et al. | |
| 2017/0315208 A1* | 11/2017 | Sadr | G01S 5/0263 |
| 2017/0322939 A1 | 11/2017 | Byron et al. | |
| 2017/0359666 A1 | 12/2017 | Lyren et al. | |
| 2018/0074785 A1 | 3/2018 | Ohmura | |
| 2018/0091782 A1 | 3/2018 | Bashkin | |
| 2018/0199123 A1 | 7/2018 | Rao et al. | |
| 2018/0218080 A1 | 8/2018 | Krishnamurthy et al. | |
| 2018/0232201 A1 | 8/2018 | Holtmann | |
| 2018/0232563 A1 | 8/2018 | Albadawi et al. | |
| 2018/0232571 A1 | 8/2018 | Bathiche et al. | |
| 2018/0232608 A1 | 8/2018 | Pradeep et al. | |
| 2018/0232645 A1 | 8/2018 | Finkelstein et al. | |
| 2018/0232662 A1 | 8/2018 | Solomon et al. | |
| 2018/0232902 A1 | 8/2018 | Albadawi et al. | |
| 2018/0233132 A1 | 8/2018 | Herold et al. | |
| 2018/0233139 A1 | 8/2018 | Finkelstein et al. | |
| 2018/0233140 A1 | 8/2018 | Koishida et al. | |
| 2018/0233141 A1 | 8/2018 | Solomon et al. | |
| 2018/0233142 A1 | 8/2018 | Koishida et al. | |
| 2018/0233145 A1 | 8/2018 | Bathiche et al. | |
| 2018/0260680 A1 | 9/2018 | Finkelstein et al. | |
| 2018/0293221 A1 | 10/2018 | Finkelstein et al. | |
| 2018/0314689 A1 | 11/2018 | Wang et al. | |
| 2019/0057703 A1 | 2/2019 | Zeinstra | |
| 2020/0012906 A1 | 1/2020 | Albadawi et al. | |
| 2020/0042839 A1 | 2/2020 | Herold et al. | |

FOREIGN PATENT DOCUMENTS

| | | |
|---|---|---|
| KR | 1020070016280 A | 2/2007 |
| WO | 2007018523 A2 | 2/2007 |
| WO | 2010104772 A1 | 9/2010 |
| WO | 2013061268 A2 | 5/2013 |
| WO | 2015012449 A1 | 1/2015 |
| WO | 2016114922 A1 | 7/2016 |
| WO | 2016162678 A1 | 10/2016 |
| WO | 2016205419 A1 | 12/2016 |

OTHER PUBLICATIONS

Kang, et al., "Detection and Tracking of Moving Objects from Overlapping EO and IR Sensors", Joint IEEE Workshop. IRIS, Computer Vision Group, University of Southern California. 2004. 6 pages.

Liu, Tian-Jian, "Reliable Multiple Object Tracking under Heavy Occlusions", Intelligence Information Processing and Trusted Computing (IPTC), 2010 International Symposium. Oct. 28-29, 2010. 3 pages.

Pan, et al., "Robust Occlusion Handling in Object Tracking", Fudan University, 2007. 8 pages.

Wagner, Martin, "Tracking with Multiple Sensors", Faculty of Computer Science at the Technical University of Munich, Sep. 12, 2004. 202 pages.

"Final Office Action Issued in U.S. Appl. No. 15/640,251", dated Apr. 2, 2019, 22 Pages.

Miro, et al., "Speaker Diarization: A review of Recent Research", In the Proceedings of IEEE Transactions on Audio, Speech and Language Processing, vol. 20, Issue 2, Feb. 1, 2012, 15 Pages.

Moattar, et al., "A Review on Speaker Diarization Systems and Approaches", In the Publication of Speech Communication, vol. 54, Issue 10, Dec. 12, 2010, 39 Pages.

"International Search Report & Written Opinion for PCT Patent Application No. PCT/US2018/062384", dated Feb. 15, 2019, 12 Pages.

Yu, et al., "Smart Meeting Systems: A Survey of State of the Art and Open Issues", In the Proceedings of ACM Computing Surveys, vol. 42, No. 2, Mar. 5, 2010, 20 Pages.

"Amazon Alexa's 'Follow-Up Mode' enables successive requests without trigger word", Retrieved from: https://appleinsider.com/articles/18/03/09/amazon-alexas-follow-up-mode-enables-successive-requests-without-trigger-word, Mar. 9, 2018, 7 Pages.

"Multiple Agents (each trained for different domain) for One Chat Bot?", Retrieved from: https://discuss.api.ai/t/multiple-agents-each-trained-for-different-domain-for-one-chat-bot/1002, Jul. 1, 2016, 1 Page.

"SARA: The Socially Aware Robot Assistant", Retrieved from: https://web.archive.org/web/20160707141922/http:/articulab.hcii.cs.cmu.edu:80/projects/sara/, Jul. 7, 2017, 10 Pages.

Arsikere, et al., "Computationally-efficient Endpointing Features for Natural Spoken Interaction with Personal-assistant Systems", In Proceedings of IEEE International Conference on Acoustics, Speech and Signal Processing, May 4, 2014, pp. 3241-3245.

Ferrer, et al., "Is the Speaker Done Yet? Faster and More Accurate End-of-Utterance Detection using Prosody", In the proceedings of Seventh International Conference on Spoken Language Processing, Sep. 16, 2002, pp. 2061-2064.

(56) References Cited

OTHER PUBLICATIONS

Kalal, et al., "Face-TLD: Tracking-Learning-Detection Applied to Caces", In Proceedings of 17th IEEE International Conference on Image Processing, Sep. 26, 2010, pp. 3789-3792.

Kozhaya, Joe, "10 Steps to Train an Effective Chatbot and its Machine Learning Models", Retrieved from: https://developer.ibm.com/dwblog/2016/10-steps-train-chat-bot-chatbot-machine-learning/, Dec. 12, 2016, 7 Pages.

Lacharite, Noelle, "Updated: Alexa Skills Kit Fact Template: Step-by-Step Guide to Build a Fact Skill", Retrieved from: https://developer.amazon.com/blogs/post/Tx3DVGG0K0TPUGQ/New-Alexa-Skills-Kit-Template:-Step-by-Step-Guide-to-Build-a-Fact-Skill, Mar. 29, 2016, 33 Pages.

Li, Bo, "A Multiple-Camera System Calibration Toolbox Using a Feature Descriptor-based Calibration Pattern", In Proceedings of IEEE International Conference on Intelligent Robots and Systems, Nov. 3, 2013, pp. 1301-1307.

Mengusoglu, Erhan, "Confidence Measures for Speech/Speaker Recognition and Applications on Turkish LVCSR", Retrieved from https://web.archive.org/web/20040619044603/http://www.tcts.fpms.ac.be/publications/phds/mengusoglu/thesis_mengus.pdf, Apr. 20, 2004, 143 Pages.

Mikolajczyk, K, et al., "Face Detection and Tracking in a Video by Propagating Detection Probabilities", In Proceedings of IEEE Transactions on Pattern Analysis and Machine Intelligence, vol. 25, Issue 10, Oct. 1, 2003, pp. 1215-1228.

Panzarino, Matthew, "Here's An Actual 3D Indoor Map of a Room Captured With Google's Project Tango Phone", Retrieved From: https://techcrunch.com/2014/02/21/heres-an-actual-3d-indoor-map-of-a-room-captured-with-googles-project-tango-phone/, Feb. 21, 2014, 6 Pages.

"International Search Report and Written Opinion Issued in PCT Application No. PCT/US2018/017139", dated May 8, 2018, 13 Pages.

"International Search Report and Written Opinion Issued in PCT Application No. PCT/US2018/017140", dated May 18, 2018, 12 Pages.

"International Search Report and Written Opinion Issued in PCT Application No. PCT/US2018/017506", dated May 4, 2018, 13 Pages.

"International Search Report and Written Opinion Issued in PCT Application No. PCT/US2018/017508", dated May 8, 2018, 13 Pages.

"International Search Report and Written Opinion Issued in PCT Application No. PCT/US2018/017509", dated May 11, 2018, 11 Pages.

"International Search Report and Written Opinion Issued in PCT Application No. PCT/US2018/017510", dated Apr. 20, 2018, 14 Pages.

"International Search Report and Written Opinion Issued in PCT Application No. PCT/US2018/017511", dated May 17, 2018, 12 Pages.

"Interntional Search Report and Written Opinion Issued in PCT Application No. PCT/US2018/017512", dated May 4, 2018, 15 Pages.

"International Search Report and Written Opinion Issued in PCT Application No. PCT/US2018/017513", dated Apr. 12, 2018, 15 Pages.

"International Search Report and Written Opinion Issued in PCT Application No. PCT/US2018/017514", dated May 17, 2018, 12 Pages.

"International Search Report and Written Opinion Issued in PCT Application No. PCT/US2018/017515", dated May 9, 2018, 12 Pages.

"International Search Report and Written Opinion Issued in PCT Application No. PCT/US2018/017517", dated May 11, 2018, 12 Pages.

Porcheron, et al., "Do Animals Have Accents?: Talking with Agents in Multi-Party Conversation", In Proceedings of 20th ACM Conference on Computer-Supported cooperative Work and Social Computing, Feb. 25, 2017, 14 Pages.

Pullen, John Patrick., "Amazon Echo Tip: How to Add Multiple Users ! Time", Retrieved from http://time.com/4668359/amazon-echo-alexa-multiple-accounts/, Feb. 13, 2017., 3 Pages.

Xiang, Li, "Improving Knowledge Base Population With Information Extraction", A Thesis Submitted in Partial fulfillment of the Requirements of the University of New York for the Degree of Doctor of Philosophy, May 2016, 131 Pages.

Yamamoto, S, et al., "Algorithm Optimizations for Low-Complexity Eye Tracking", In Proceedings of IEEE International Conference on Systems, Man, and Cybernetics, Oct. 2009, pp. 18-22.

Yun-Nung, Chen, "Unsupervised Learning and Modeling of Knowledge and Intent for Spoken Dialogue Systems", In Proceedings of the 53rd Annual Meeting of the Association for Computational Linguistics, Jul. 28, 2015, 8 Pages.

Zhang, et al., "A Joint Model of Intent Determination and Slot Filling for Spoken Language Understanding", In Proceedings of the Twenty-Fifth International Joint Conference on Artificial Intelligence, Jul. 9, 2016, pp. 2993-2999.

"Train the Natural Language Processing Classifiers", Retrieved From <<https://www.mindmeld.com/docs/train_the_natural_language_processing_classifiers.html>>, Retrieved on: May 2, 2017, 10 Pages.

"Using Multiple Alexa Devices", Retrieved From <21 https://www.amazon.com/gp/help/customer/display.html?nodeId=202013740>>, Apr. 24, 2017, 2 Pages.

"Application Filed in U.S. Appl. No. 15/173,349", filed Jun. 3, 2016, 34 Pages.

"Application Filed in U.S. Appl. No. 15/395,961", filed Dec. 30, 2016, 79 Pages.

Beltagy, et al., "Improved Semantic Parsers for If-Then Statements", In Proceedings of the 54th Annual Meeting of the Association for Computational Linguistics, vol. 1, Aug. 7, 2016, pp. 726-736.

Boakye, et al., "Overlapped Speech Detection for Improved Speaker Diarization in Multiparty Meetings", In Proceedings of IEEE International Conference on Acoustics, Speech and Signal Processing, Mar. 31, 2008, 4 Pages.

Zotkin, et al., "Joint Audio-Visual Tracking Using Particle Filters", In EURASIP Journal on Applied Signal Processing, vol. 2002, Issue 1, Jan. 2002, pp. 1154-1164.

Fossard, et al., "Between Anaphora and Deixis . . . The Resolution of the Demonstrative Noun Phrase that N", In Journal of Language and Cognitive Processes, vol. 27, Issue 9, Nov. 2, 2011, 3 Pages.

Gebhart, Andrew, "How to bring Alexa into every room of your home", Retrieved From <<https://www.cnet.com/how-to/how-to-install-alexa-in-every-room-of-your-home/>>, Feb. 2, 2017, 8 Pages.

Goncalves, et al., "Assessing Users' Emotion At Interaction Time: A Multimodal Approach With Multiple Sensors", In Proceedings of Soft Computing, vol. 21, Issue 18, Mar. 21, 2016, 8 Pages.

Goswami, et al., "A Reviewon Low Light Image Enhancement Using Image Processing Technique", In International Journal of Technical Research, vol. 5, Issue 1, Mar. 2016, pp. 60-62.

He, et al., "Sensor scheduling for target tracking: A Monte Carlo sampling approach", In Journal of Digital Signal Processing, vol. 16, Issue 5, Sep. 2006, pp. 533-545.

Huijbregts, et al., "Speech Overlap Detection in a Two-Pass Speaker Diarization System", In Proceedings of 10th Annual Conference of the International Speech Communication, Sep. 6, 2009, pp. 1063-1066.

Kabadjov, Mijail Alexandrov., "A Comprehensive Evaluation of Anaphora Resolution and Discourse-new classification", In thesis of University of Essex, May 2007, 266 Pages.

Wheeler, et al., "Face Recognition at a Distance", In Publication of Springer, Jan. 2011, pp. 353-381.

Toutanova, et al., "Compositional Learning of Embeddings for Relation Paths in Knowledge Bases and Text", In Proceedings of the 54th Annual Meeting of the Association for Computational Linguistics, Aug. 7, 2016, pp. 1434-1444.

(56) References Cited

OTHER PUBLICATIONS

MK, et al., "Ambiguities in Natural Language Processing", In International Journal of Innovative Research in Computer and Communication Engineering, vol. 2, Special Issue 5, Oct. 2014, pp. 392-394.

Sinha, et al., "An Analysis Engine for Dependable Elicitation on Natural Language Use Case Description and its Application to Industrial Use Cases", In IBM Research Report, RC242712, Dec. 18, 2008, 12 Pages.

Quirk, et al., "Language to Code: Learning Semantic Parsers for If-This-Then-That Recipes", In Proceedings of the 53rd Annual Meeting of the Association for Computational Linguistics, Jul. 26, 2015, pp. 878-888.

Rizwan, et al., "Local Enhancement for Robust Face Detection in Poor SNR Images", In International Journal of Computer Science and Network Security, vol. 9, Issue 6, Jun. 2009, pp. 93-96.

Ballan, et al., "Event Detection and Recognition for Semantic Annotation of Video", In Journal of Multimedia Tools and Applications, vol. 51, Issue 1, Nov. 10, 2010, pp. 279-302.

"Non Provisional Application Filed in U.S. Appl. No. 15/885,518", filed Jan. 31, 2018, 40 Pages.

"Non Final Office Action Issued in U.S. Appl. No. 15/636,422", dated Sep. 4, 2018, 11 Pages.

"Non Final Office Action Issued in U.S. Appl. No. 15/640,251", dated Oct. 15, 2018, 22 Pages.

"Non Final Office Action Issued in U.S. Appl. No. 15/646,871", dated Dec. 19, 2018, 22 Pages.

"Non Final Office Action Issued in U.S. Appl. No. 15/656,994", dated Jan. 22, 2019, 8 Pages.

"Non Final Office Action Issued in U.S. Appl. No. 15/657,031", dated Oct. 5, 2018, 16 Pages.

"Non Final Office Action Issued in U.S. Appl. No. 15/832,656", dated Feb. 7, 2019, 8 Pages.

"Non Final Office Action Issued in U.S. Appl. No. 15/657,822", dated Feb. 21, 2019, 25 Pages.

Constine, "Instagram launches selfie filters, copying the last big Snapchat feature", Retrieved from https://techcrunch.com/2017/05/16/instagram-face-filters/, May 16, 2017, 8 Pages.

"International Search Report and Written Opinion Issued in PCT Application No. PCT/US2019/022836", dated Jun. 24, 2019, 15 Pages.

"International Search Report and Written Opinion Issued No. PCT Application No. PCT/US2019/029558", dated Jun. 28, 2019, 10 Pages.

"Final Office Action Issued in U.S. Appl. No. 15/646,871", dated Apr. 19, 2019, 22 Pages.

"Non Final Office Action Issued in U.S. Appl. No. 15/682,425", dated May 6, 2019, 12 Pages.

"Non-Final Office Action Issued in U.S. Appl. No. 15/646,871", dated Sep. 3, 2019, 23 Pages.

"Final Office Action Issued in U.S. Appl. No. 15/832,656", dated Aug. 23, 2019, 10 Pages.

"Final Office Action Issued in U.S. Appl. No. 15/657,822", dated Aug. 22, 2019, 22 Pages.

"Non Final Office Action Issued in U.S. Appl. No. 15/640,251", dated Sep. 12, 2019, 21 Pages.

"Notice of Allowance Issued in U.S. Appl. No. 16/573,677", dated Nov. 6, 2019, 9 Pages.

"Non Final Office Action Issued in U.S. Appl. No. 15/657,822", dated Feb. 6, 2020, 25 Pages.

"Non Final Office Action Issued in U.S. Appl. No. 15/832,656", dated Jan. 6, 2020, 9 Pages.

"Final Office Action Issued in U.S. Appl. No. 15/646,871", dated Jan. 21, 2020, 23 Pages.

"Final Office Action Issued in U.S. App. No. 15/640,251", dated Jan. 30, 2020, 21 Pages.

"Non Final Office Action Issued in U.S. Appl. No. 16/005,470", dated Feb. 24, 2020, 11 Pages.

* cited by examiner

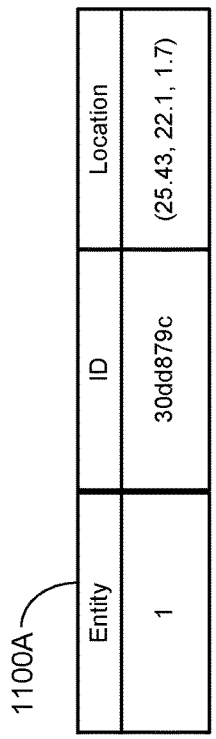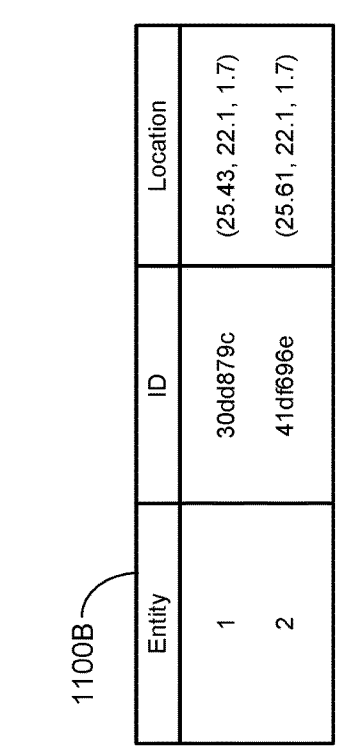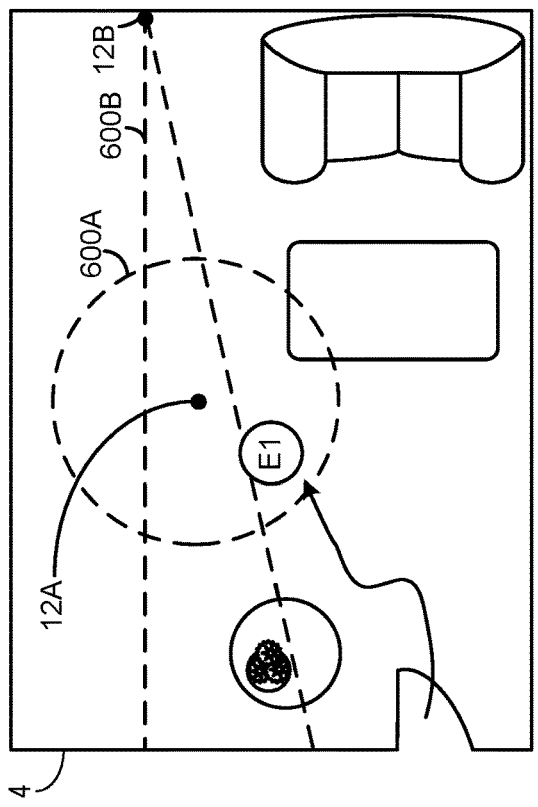
FIG. 13A
FIG. 13B

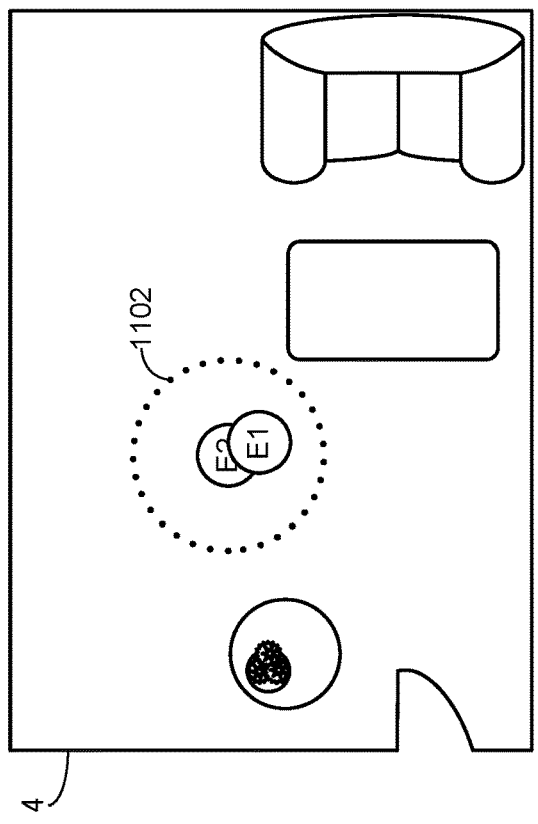
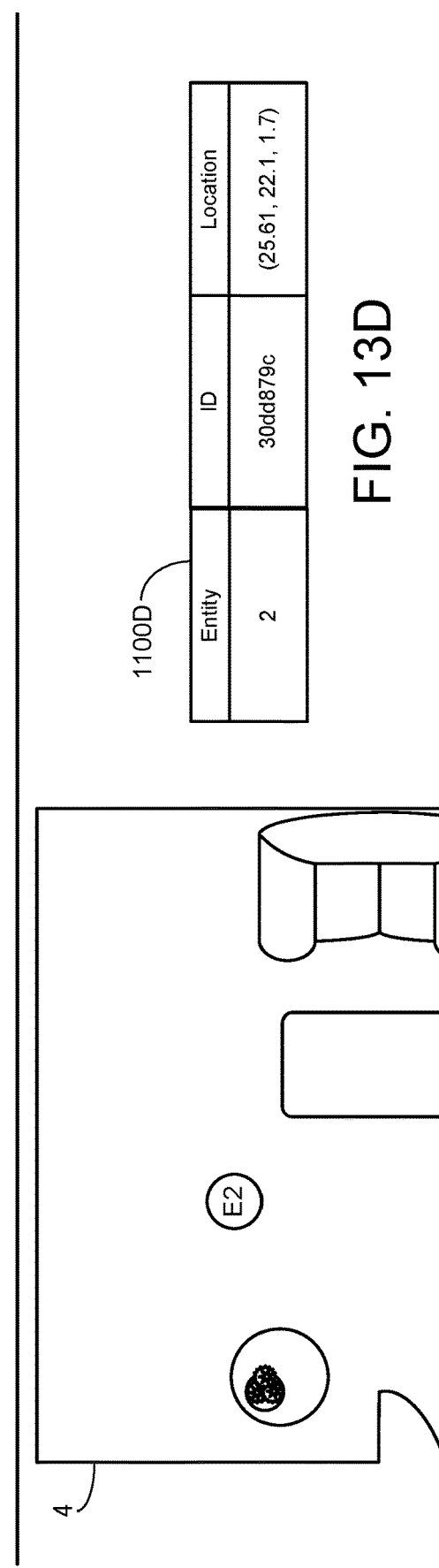
FIG. 13C
FIG. 13D

ENTITY-TRACKING COMPUTING SYSTEM

CROSS REFERENCE TO RELATED APPLICATIONS

This application claims priority to U.S. Provisional Patent Application No. 62/459,020 filed Feb. 14, 2017, and to U.S. Provisional Patent Application No. 62/482,165 filed Apr. 5, 2017, the entirety of which are hereby incorporated herein by reference.

BACKGROUND

Interacting with computing systems via natural interactions, such as one or more of voice recognition, text, gesture recognition, motion detection, gaze detection, intent recognition, brain activity assessment, text, the state of a home automated device, etc., enables natural user interface experiences. Such natural user interface experiences can be augmented when the computing systems have information regarding positions and movements of the humans they are interacting with.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

An entity-tracking computing system receives sensor information from a plurality of different sensors. The positions of entities detected by the various sensors are resolved to an environment-relative coordinate system so that entities identified by one sensor can be tracked across the fields of detection of other sensors.

BRIEF DESCRIPTION OF THE DRAWINGS

FIGS. 13A-13D schematically illustrate determining that an environment-relative position of a second entity is consistent with an environment-relative position of a first entity.

DETAILED DESCRIPTION

Tracking of entities (e.g., humans, pets, autonomous robots) in an environment can be complicated when relying on multiple independent sensors having different physical locations, hardware capabilities, fields-of-detection (FODs), etc. For example, the same entity may be detected at the same position by multiple sensors, and recorded by an entity-tracking computing system as multiple different entities. Similarly, an entity may move from the FOD of one sensor to the FOD of another sensor. Based on data received from the sensors, the entity-tracking computing system may be unaware that both sensors have detected the same entity, particularly when one of the sensors lacks the ability to positively identify the entity.

Accordingly, the present disclosure is directed to techniques for tracking entities in an environment via a plurality of sensors. The entity-tracking techniques discussed herein are primarily described from the perspective of an entity-tracking computing system, which may be implemented as any suitable computing device or combination of computing devices. For example, tracking of entities in an environment may be performed by various smart assistant devices, security devices, home automation devices, etc. Specifically, and as will be described below, in some cases an entity-tracking computing system may be implemented as part of smart assistant device configured to interpret and respond to natural language inputs, for example by answering questions or performing actions.

Figure 1:
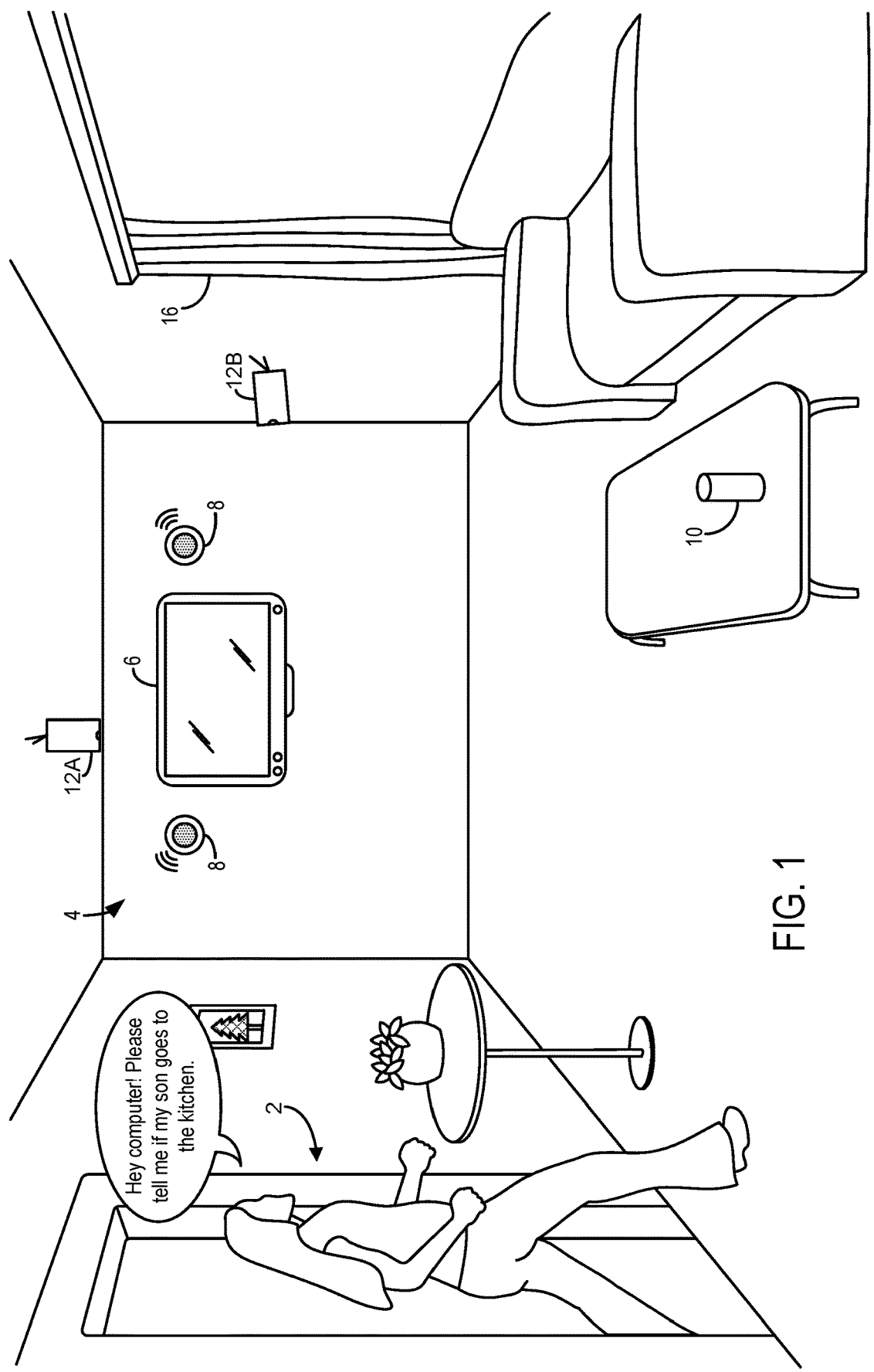
FIG. 1 shows an example environment with a smart assistant computer in the form of an all-in-one computing device according to an example of the present disclosure.

FIG. 1 illustrates a human 2 entering a living room 4 with one example of a smart assistant device in the form of an all-in-one computing device 10. As described in more detail below, in some examples computing device 10 may be configured to receive and process natural language inputs. A user may utilize the smart assistant device for myriad functions. For example, the user may provide natural language input to ask the smart assistant device to perform a variety of tasks, such as provide information, change the state of a device, send a message, complete a purchase, etc. In another example, tasks may be performed programmatically without input from the user. For example, computing device 10 may utilize sensor data, such as audio and/or video data, for example received from cameras 12A and/or 12B, to detect when the user moves to another room and is looking at or "engaged" with another device. Using this data, computing device 10 may automatically alter the state of the device accordingly.

The user may ask the system for information about a wide range of topics, such as the weather, personal calendar events, movie show times, etc. In some examples, the smart assistant device also may be configured to control elements in the living room 4, such as a television 6, speakers 8 of a music system, or motorized curtains 16.

The smart assistant device also may be utilized to receive and store messages and/or reminders to be delivered at an appropriate future time. Using data received from sensors, the smart assistant device may track and/or communicate with one or more users or other entities.

In some examples, the computing device 10 may be operatively connected with one or more other computing devices using a wired connection, or may employ a wireless connection via Wi-Fi, Bluetooth, or any other suitable wireless communication protocol. For example, the computing device 10 may be communicatively coupled to one or more other computing devices via a network. The network may take the form of a local area network (LAN), wide area network (WAN), wired network, wireless network, personal area network, or a combination thereof, and may include the Internet. Additional details regarding components and computing aspects of the computing device 10 are described in more detail below with reference to FIG. 18.

Figure 15:
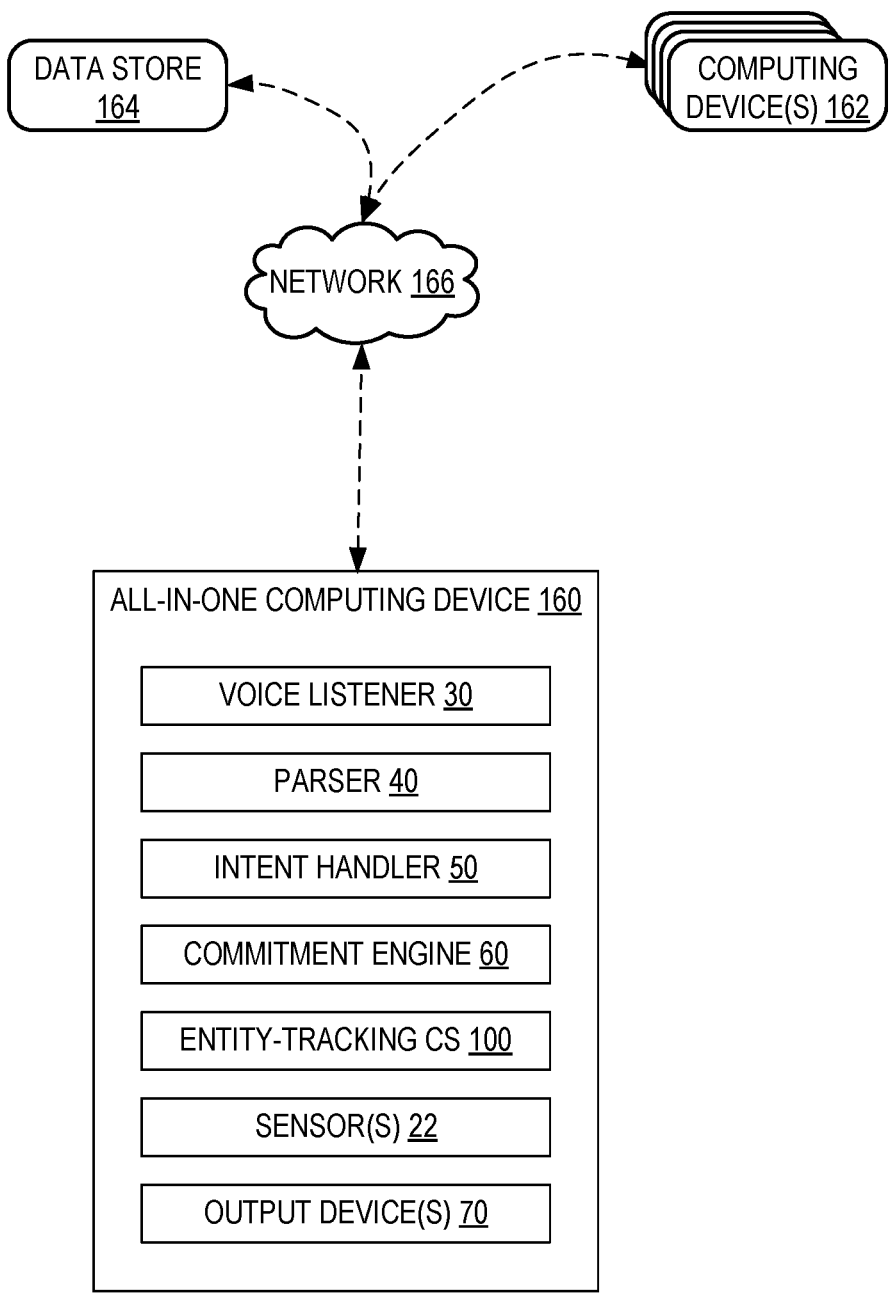
FIG. 15 schematically shows an all-in-one computing device that implements a smart assistant computer according to examples of the present disclosure.
Figure 16:
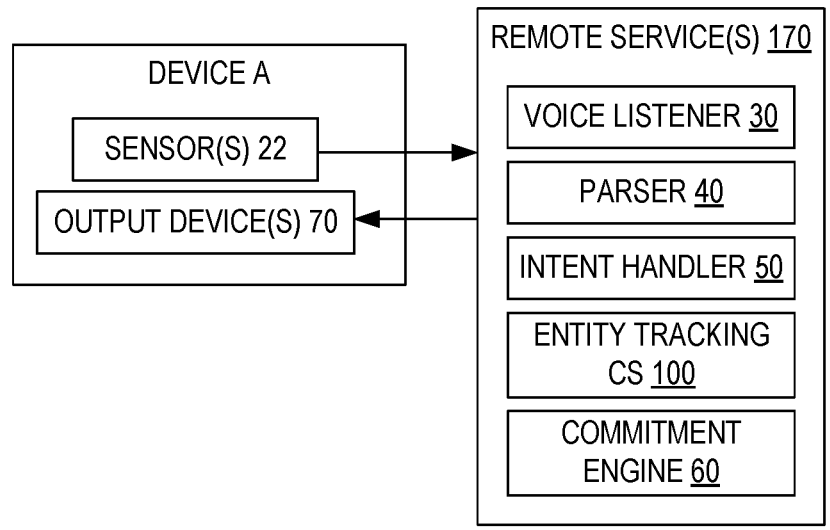
FIG. 16 schematically shows an example implementation in which one or more remote services perform functionality of the smart assistant computer according to examples of the present disclosure.
Figure 17:
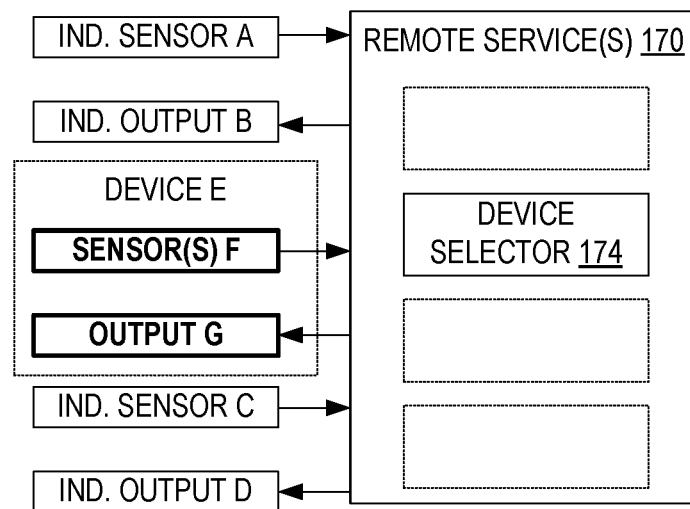
FIG. 17 schematically shows another example implementation in which one or more remote services perform functionality of a smart assistant computer according to examples of the present disclosure.

It will be appreciated that the computing device 10 of FIG. 1 is merely one example implementation of the entity-tracking computing system of the present disclosure. Additional example implementations across two or more devices are illustrated in FIGS. 15-17 and described in more detail below.

Figure 2:
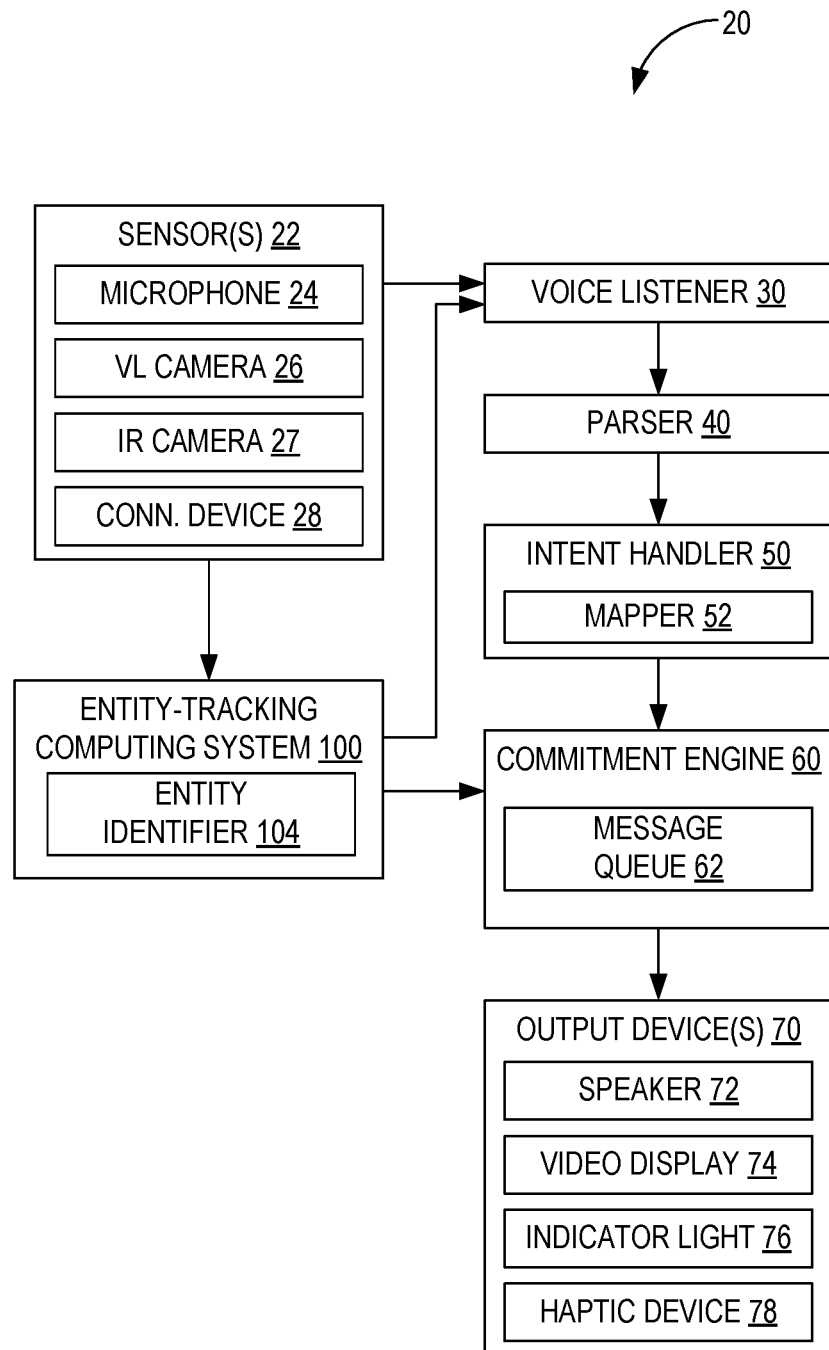
FIG. 2 schematically shows an example logical architecture for implementing a smart assistant computer according to an example of the present disclosure.

FIG. 2 shows an example logical architecture for implementing a smart assistant device 20 capable of recognizing and responding to natural language inputs according to examples of the present disclosure. As described in more detail below, in various examples the system 20 may be implemented in a single computing device, across two or more devices, in a cloud-supported network, and in combinations of the foregoing.

In this example the smart assistant device 20 includes at least one sensor 22, an entity-tracking computing system 100, a voice listener 30, a parser 40, an intent handler 50, a commitment engine 60, and at least one output device 70. In some examples the sensors 22 may include one or more microphones 24, visible light cameras 26, infrared cameras 27, and connectivity devices 28, such as Wi-Fi or Bluetooth modules. In some examples sensor(s) 22 may comprise stereoscopic and/or depth cameras, head trackers, eye trackers, accelerometers, gyroscopes, gaze detection devices, electric-field sensing componentry, GPS or other location tracking devices, temperature sensors, device state sensors, and/or any other suitable sensor.

The entity-tracking computing system 100 is configured to detect entities and their activities, including people, animals, or other living things, as well as non-living objects. Entity-tracking computing system 100 includes an entity identifier 104 that is configured to recognize individual users and/or non-living objects. Voice listener 30 receives audio data and utilizes speech recognition functionality to translate spoken utterances into text. Voice listener 30 also may assign confidence value(s) to the translated text, and may perform speaker recognition to determine an identity of the person speaking, as well as assign probabilities to the accuracy of such identifications. Parser 40 analyzes text and confidence values received from voice listener 30 to derive user intentions and generate corresponding machine-executable language.

Intent handler 50 receives machine-executable language representing user intentions from the parser 40, and resolves missing and ambiguous information to generate commitments. Commitment engine 60 stores commitments from the intent handler 50. At a contextually appropriate time, the commitment engine may deliver one or more messages and/or execute one or more actions that are associated with one or more commitments. Commitment engine 60 may store messages in a message queue 62 or cause one or more output devices 70 to generate output. The output devices 70 may comprise one or more of speaker(s) 72, video display(s) 74, indicator light(s) 76, haptic device(s) 78, and/or other suitable output devices. In other examples, output devices 70 may comprise one or more other devices or systems, such as home lighting, thermostats, media programs, door locks, etc., that may be controlled via actions executed by the commitment engine 60.

In different examples the voice listener 30, parser 40, intent handler 50, commitment engine 60, and/or entity-tracking computing system 100 may be embodied in software that is stored in memory and executed by one or more processors of a computing device. In some implementations, specially programmed logic processors may be utilized to increase the computational efficiency and/or effectiveness of the smart assistant device. Additional details regarding the components and computing aspects of computing devices that may store and execute these modules are described in more detail below with reference to FIG. 18.

With reference again to FIG. 2, in some examples the voice listener 30 and/or commitment engine 60 may receive context information including associated confidence values from entity-tracking computing system 100. As described in more detail below, entity-tracking computing system 100 may determine an identity, position, and/or current status of one or more entities within range of one or more sensors, and may output such information to one or more other modules, such as voice listener 30, commitment engine 60, etc. In some examples, entity-tracking computing system 100 may interpret and evaluate sensor data received from one or more sensors, and may output context information based on the sensor data. Context information may include the entity-tracking computing system's guesses/predictions as to the identity, position, and/or status of one or more detected entities based on received sensor data. In some examples, the guesses/predictions may additionally include a confidence value defining the statistical likelihood that the information is accurate.

Figure 3:
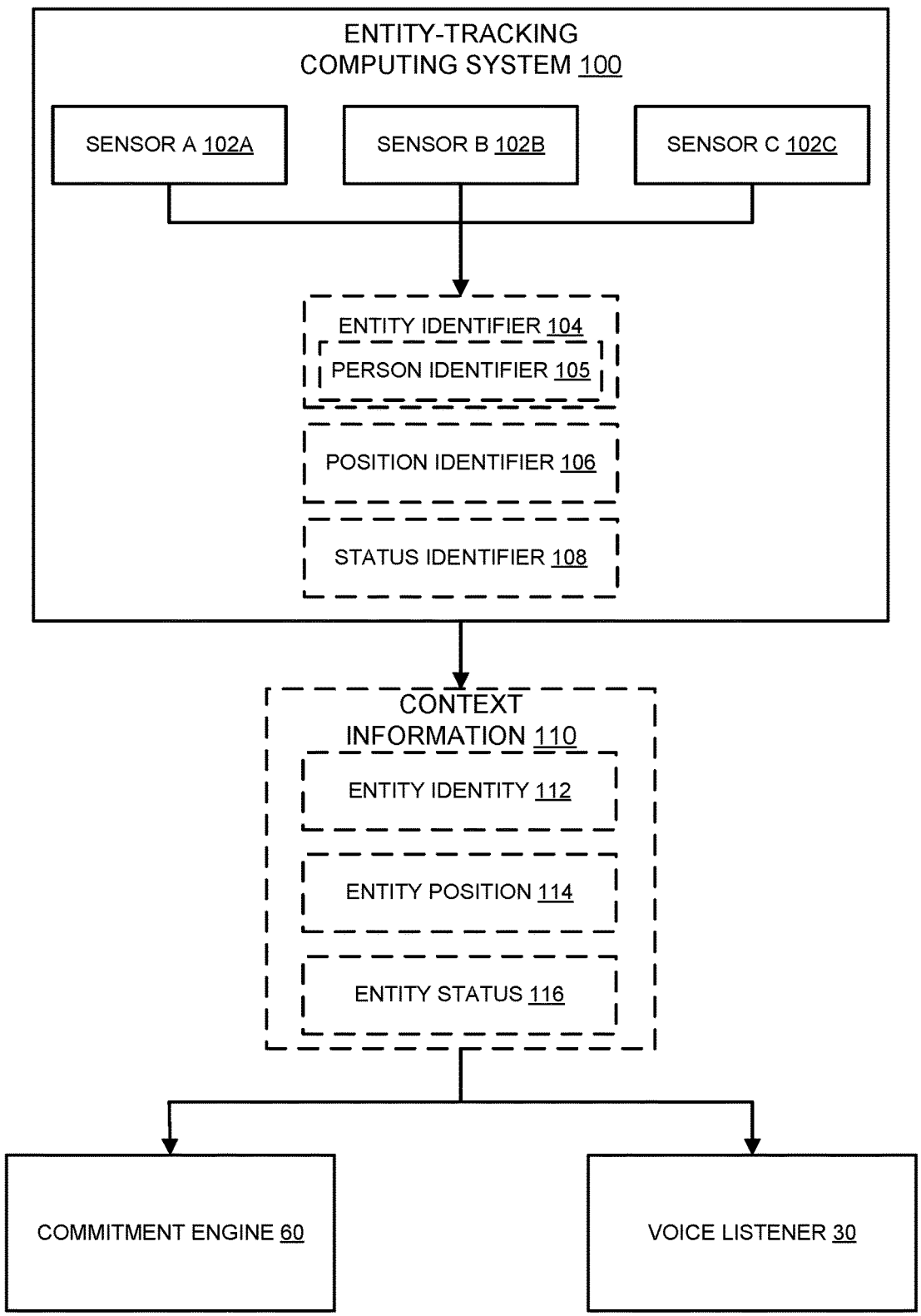
FIG. 3 schematically shows an entity-tracking computing system that may determine an identity, position, and/or current status of one or more entities according to examples of the present disclosure.

FIG. 3 schematically illustrates an example entity-tracking computing system 100 that may, in some examples, comprise a component of the smart assistant device 20. Entity-tracking computing system 100 may be used to determine an identity, position, and/or current status of one or more entities within range of one or more sensors. Entity-tracking computing system 100 may output such information to one or more other modules of smart assistant device 20, such as the commitment engine 60, voice listener 30, etc.

The word "entity" as used in the context of the entity-tracking computing system 100 may refer to people, animals, or other living things, as well as non-living objects. For example, the entity-tracking computing system may be configured to identify furniture, appliances, autonomous robots, structures, landscape features, vehicles, and/or any other physical object, and determine the position/location and current status of such physical objects. In some cases, the entity-tracking computing system 100 may be configured to only identify people and not other living or non-living things. In such cases, the word "entity" may be synonymous with the words "person" or "human."

Entity-tracking computing system 100 receives sensor data from one or more sensors 102, such as sensor A 102A, sensor B 102B, and sensor C 102C, though it will be understood that an entity-tracking computing system may be used with any number and variety of suitable sensors. As examples, sensors usable with an entity-tracking computing system may include cameras (e.g., visible light cameras, UV cameras, IR cameras, depth cameras, thermal cameras), microphones, directional microphone arrays, pressure sensors, thermometers, motion detectors, proximity sensors, accelerometers, global positioning satellite (GPS) receivers, magnetometers, radar systems, lidar systems, environmental monitoring devices (e.g., smoke detectors, carbon monoxide detectors), barometers, health monitoring devices (e.g., electrocardiographs, sphygmomanometers, electroencephalographs), automotive sensors (e.g., speedometers, odometers, tachometers, fuel sensors), and/or any other sensors or devices that collect and/or store information pertaining to the identity, position, and/or current status of one or more people or other entities. In some examples, the entity-tracking computing system 100 may occupy a common device housing with one or more of the plurality of sensors 102, and/or the entity-tracking computing system and its associated sensors may be distributed across multiple devices configured to communicate via one or more network communications interfaces (e.g., Wi-Fi adapters, Bluetooth interfaces).

As shown in the example of FIG. 3, entity-tracking computing system 100 may include an entity identifier 104, a person identifier 105, a position (location) identifier 106, and a status identifier 108. In some examples, the person identifier 105 may be a specialized component of the entity identifier 100 that is particularly optimized for recognizing people, as opposed to other creatures and non-living things. In other cases, the person identifier 105 may operate separately from the entity identifier 104, or the entity-tracking computing system 100 may not include a dedicated person identifier.

Depending on the specific implementation, any or all of the functions associated with the entity identifier, person identifier, position identifier, and status identifier may be performed by the individual sensors 102A-102C. Though the present description generally describes the entity-tracking computing system 100 as receiving data from sensors, this does not require that the entity identifier 104, as well as other modules of the entity-tracking computing system, must be implemented on a single computing device that is separate and distinct from the plurality of sensors associated with the entity-tracking computing system. Rather, functions of the entity-tracking computing system 100 may be distributed amongst the plurality of sensors, or other suitable devices. For example, rather than sending raw sensor data to the entity-tracking computing system, individual sensors may be configured to attempt to identify entities that they detect, and report this identification to the entity-tracking computing system 100, and/or other modules of smart assistant device 20. Furthermore, to simplify descriptions below, the term "sensor" is sometimes used to describe not only the physical measurement device (e.g., microphone or camera), but also the various logic processors configured and/or programmed to interpret signals/data from the physical measurement devices. For example, a "microphone" may be used to refer to the device that translates acoustic energy to an electrical signal, the analog-to-digital converter that converts the electrical signal to digital data, the on-board application-specific-integrated-circuit that pre-processes the digital data, and the downstream modules described herein (e.g., entity-tracking computing system 100, entity identifier 104, voice listener 30, or parser 40). As such, reference to a generic "sensor" or a particular sensor (e.g., "microphone" or "camera") should not be construed to mean only the physical measurement device, but also the cooperating modules/engines, which can be distributed across one or more computers.

Each of the entity identifier 104, person identifier 105, position identifier 106, and status identifier 108 is configured to interpret and evaluate sensor data received from the plurality of sensors 102, and to output context information 110 based on the sensor data. Context information 110 may include the entity-tracking computing system's guesses/predictions as to an identity, position, and/or status of one or more detected entities based on received sensor data. As will be described in more detail below, each of the entity identifier 104, person identifier 105, position identifier 106, and status identifier 108 may output their predictions/identifications along with a confidence value.

The entity identifier 104, person identifier 105, position identifier 106, status identifier 108, and other processing modules described herein may utilize one or more machine-learning technologies. Non-limiting examples of such machine-learning technologies can include Feedforward Networks, Recurrent Neural Networks (RNN), Long Short-term Memory (LSTM), Convolutional Neural Networks, Support-vector Machines (SVM), Generative-Adversarial Networks (GAN), Variational Autoencoders, Q-Learning, and Decision Trees. The various identifiers, engines, and other processing blocks described herein may be trained via supervised and/or unsupervised learning utilizing these, or any other appropriate, machine learning technologies to make the described assessments, decisions, identifications, etc. It should be understood, however, that this description is not intended to put forth new technologies for making such assessments, decisions, identifications, etc. Instead, this description is intended to manage computational resources, and as such, is meant to be compatible with any type of processing module.

The entity identifier 104 may output an entity identity 112 of a detected entity, and such entity identity may have any suitable degree of specificity. In other words, based on received sensor data, the entity-tracking computing system 100 may predict the identity of a given entity, and output such information as entity identity 112. For example, the entity identifier 104 may report that a particular entity is a piece of furniture, a dog, a human male, etc. Additionally, or alternatively, the entity identifier 104 may report that a particular entity is an oven with a particular model number; a pet dog with a specific name and breed; an owner or known user of smart assistant device 20, with the owner/known user having a particular name and profile; etc. In some examples, the degree of specificity with which the entity identifier 104 identifies/classifies detected entities may depend on one or more of user preferences and sensor limitations. In some cases, the entity identity output by the entity identifier may simply be a generic identifier that provides no information regarding the nature of the tracked entity, but rather is used to distinguish one entity from another.

When applied to people, the entity-tracking computing system 100 may in some cases collect information about individuals whom it is unable to identify by name. For example, the entity identifier 104 may record images of a person's face, and associate these images with recorded audio of the person's voice. Should the person subsequently speak to or otherwise address the smart assistant device 20, the entity-tracking computing system 100 will then have at least some information regarding with whom the smart assistant device is interacting. In some examples, the smart assistant device 20 could also prompt the person to state their name, so as to more easily identify the person in the future.

In some examples, the smart assistant device 20 may utilize a person's identity to customize a user interface for the person. In one example, a user may be identified who has limited visual capabilities. In this example and based on this identification, a display of the smart assistant device 20 (or other device with which the user is interacting) may be modified to display larger text, or to provide a voice-only interface.

The position identifier 106 may be configured to output an entity position (i.e., location) 114 of a detected entity. In other words, the position identifier 106 may predict the current position of a given entity based on collected sensor data, and output such information as entity position 114. As with the entity identity 112, the entity position 114 may have any suitable level of detail, and this level of detail may vary with user preferences and/or sensor limitations. For example, the position identifier 106 may report that a detected entity has a two-dimensional position defined on a plane such as a floor or wall. Additionally, or alternatively, the reported entity position 114 may comprise a three-dimensional position of a detected entity within a real world, three-dimensional environment. In some examples an entity position 114 may comprise a GPS position, a location within an environment-relative coordinate system, etc.

The reported entity position 114 for a detected entity may correspond to the entity's geometric center, a particular part of the entity that is classified as being important (e.g., the head of a human), a series of boundaries defining the borders of the entity in three-dimensional space, etc. The position identifier 106 may further calculate one or more additional parameters describing the position and/or orientation of a detected entity, such as a pitch, roll, and/or yaw parameter. In other words, the reported position of a detected entity may have any number of degrees-of-freedom, and may include any number of coordinates defining the position of the entity in an environment. In some examples, an entity position 114 of a detected entity may be reported even if the entity-tracking computing system 100 is unable to identify the entity, and/or determine the current status of the entity.

Status identifier 108 may be configured to output an entity status 116 of a detected entity. In other words, the entity-tracking computing system 100 may be configured to predict the current status of a given entity based on received sensor data, and output such information as entity status 116. "Entity status" can refer to virtually any measurable or classifiable property, activity, or behavior of a given entity. For example, when applied to a person, the entity status of the person can indicate a posture of the person (e.g., standing, sitting, laying down), a speed at which the person is walking/running, a current activity of the person (e.g., sleeping, watching TV, working, playing a game, swimming, talking on the phone), a current mood of the person (e.g., by evaluating the person's facial expression or tone of voice), biological/physiological parameters of the person (e.g., the person's heart rate, respiration rate, oxygen saturation, body temperature, neurological activity), whether the person has any current or upcoming calendar events/appointments, etc. "Entity status" can refer to additional/alternative properties or behaviors when applied to other creatures or non-living objects, such as a current temperature of an oven or kitchen sink, whether a device (e.g., television, lamp, microwave) is powered on, whether a door is open, etc.

In some examples, the status identifier 108 may use sensor data to calculate a variety of different biological/physiological parameters of a human. This may be done in a variety of suitable ways. For example, the entity-tracking computing system 100 may be configured to interface with an optical heart rate sensor, a pulse oximeter, a sphygmomanometer, electrocardiograph, etc. Additionally or alternatively, the status identifier 108 may be configured to interpret data from one or more cameras and/or other sensors in an environment, and process the data in order to calculate a human's heart rate, respiration rate, oxygen saturation, etc. For example, the status identifier 108 may be configured to utilize Eulerian magnification and/or similar techniques to amplify miniscule movements or changes captured by the cameras, thereby allowing the status identifier to visualize the flow of blood through a human's circulatory system and calculate associated physiological parameters. Such information can be used, for example, to determine when the person is asleep, working out, in distress, experiencing health problems, etc.

Upon determining one or more of the entity identity 112, entity position 114, and entity status 116, such information may be sent as context information 110 to any of a variety of external modules or devices, where it may be used in a variety of ways. For example, context information 110 may be used by commitment engine 60 to manage commitments and associated messages and notifications. In some examples, context information 110 may be used by commitment engine 60 to determine whether a particular message, notification, or commitment should be executed and/or presented to a user. Similarly, context information 110 may be utilized by voice listener 30 when interpreting human speech or activating functions in response to a keyword trigger.

As noted above, in some examples the entity-tracking computing system 100 may be implemented in a single computing device. In other examples, one or more functions of the entity-tracking computing system 100 may be distributed across multiple computing devices working cooperatively. For example, one or more of the entity identifier 104, person identifier 105, position identifier 106, and status identifier 108 may be implemented on different computing devices, while still collectively comprising an entity-tracking computing system configured to perform the functions described herein. As indicated above, any or all of the functions of the entity-tracking computing system may be performed by individual sensors 102. Further, in some examples entity-tracking computing system 100 may omit one or more of the entity identifier 104, person identifier 105, position identifier 106, and status identifier 108, and/or include one or more additional components not described herein, while still providing context information 110. Additional details regarding components and computing aspects that may be used to implement entity-tracking computing system 100 are described in more detail below with respect to FIG. 18.

Each of entity identity 112, entity position 114, and entity status 116 may take any suitable form. For example, each of the entity identity 112, position 114, and status 116 may take the form of a discrete data packet including a series of values and/or labels describing the information gathered by the entity-tracking computing system. Each of the entity identity 112, position 114, and status 116 may additionally include a confidence value defining a statistical likelihood that the information is accurate. For example, if the entity identifier 104 receives sensor data that strongly indicates that a particular entity is a human male named "John Smith," then entity identity 112 may include this information along with a corresponding relatively high confidence value, such as 90% confidence. If the sensor data is more ambiguous, then the confidence value included in entity identity 112 correspondingly may be relatively lower, such as 62%. In some examples, separate predictions may be assigned separate confidence values. For example, the entity identity 112 may indicate with 95% confidence that a particular entity is a human male, and indicate with a 70% confidence that the entity is John Smith. Such confidence values (or probabilities) may be utilized by a cost function in generating cost calculations for providing messages or other notifications to a user and/or performing action(s).

In some implementations, the entity-tracking computing system 100 may be configured to combine or fuse data from multiple sensors in order to output more accurate predictions. As an example, a camera may locate a person in a particular room. Based on the camera data, the entity-tracking computing system 100 may identify the person with a confidence value of 70%. However, the entity-tracking computing system 100 may additionally receive recorded speech from a microphone. Based on the recorded speech alone, the entity-tracking computing system 100 may identify the person with a 60% confidence value. By combining the data from the camera with the data from the microphone, the entity-tracking computing system 100 may identify the person with a higher confidence value than would be possible using the data from either sensor alone. For example, the entity-tracking computing system may determine that the recorded speech received from the microphone corresponds to lip movements of the person visible to the camera when the speech was received, and thereby conclude with relatively high confidence, such as 92%, that the person visible to the camera is the person speaking. In this manner, the entity-tracking computing system 100 may combine the confidence values of two or more predictions to identify a person with a combined, higher confidence value.

In some examples, data received from various sensors may be weighted differently depending upon a reliability of the sensor data. This can be especially relevant in situations where multiple sensors are outputting seemingly inconsistent data. In some examples, the reliability of a sensor's data may be based at least in part on the type of data generated by the sensor. For example, in some implementations a reliability of video data may be weighted higher than a reliability of audio data, as the presence of an entity on camera may be a better indicator of its identity, position, and/or status than recorded sounds that are presumed to originate from the entity. It will be appreciated that a reliability of sensor data is a different factor than a confidence value associated with a predicted accuracy of an instance of data. For example, several instances of video data may have different confidence values based on different contextual factors present at each instance. Each of these instances of video data, however, may be associated with a single reliability value for video data in general.

In one example, data from a camera may suggest that a particular person is in a kitchen with a 70% confidence value, such as via face recognition analysis. Data from a microphone may suggest with a 75% confidence value that the same person is in a nearby hallway, such as via voice recognition analysis. Even though the instance of microphone data carries a higher confidence value, the entity-tracking computing system 100 may output a prediction that the person is in the kitchen based on a higher reliability of the camera data as compared to a lower reliability of the microphone data. In this manner and in some examples, different reliability values for different sensor data may be used along with confidence values to reconcile conflicting sensor data and determine an identity, position, and/or status of an entity.

Additionally, or alternatively, more weight may be given to sensors that have higher precision, more processing power or otherwise greater capabilities. For example, a professional-grade video camera may have a significantly improved lens, image sensor, and digital image processing capabilities as compared to a basic webcam found in a laptop. Accordingly, a higher weight/reliability value may be given to video data received from the professional-grade camera as compared to the webcam, as such data is likely to be more accurate.

Figure 4:
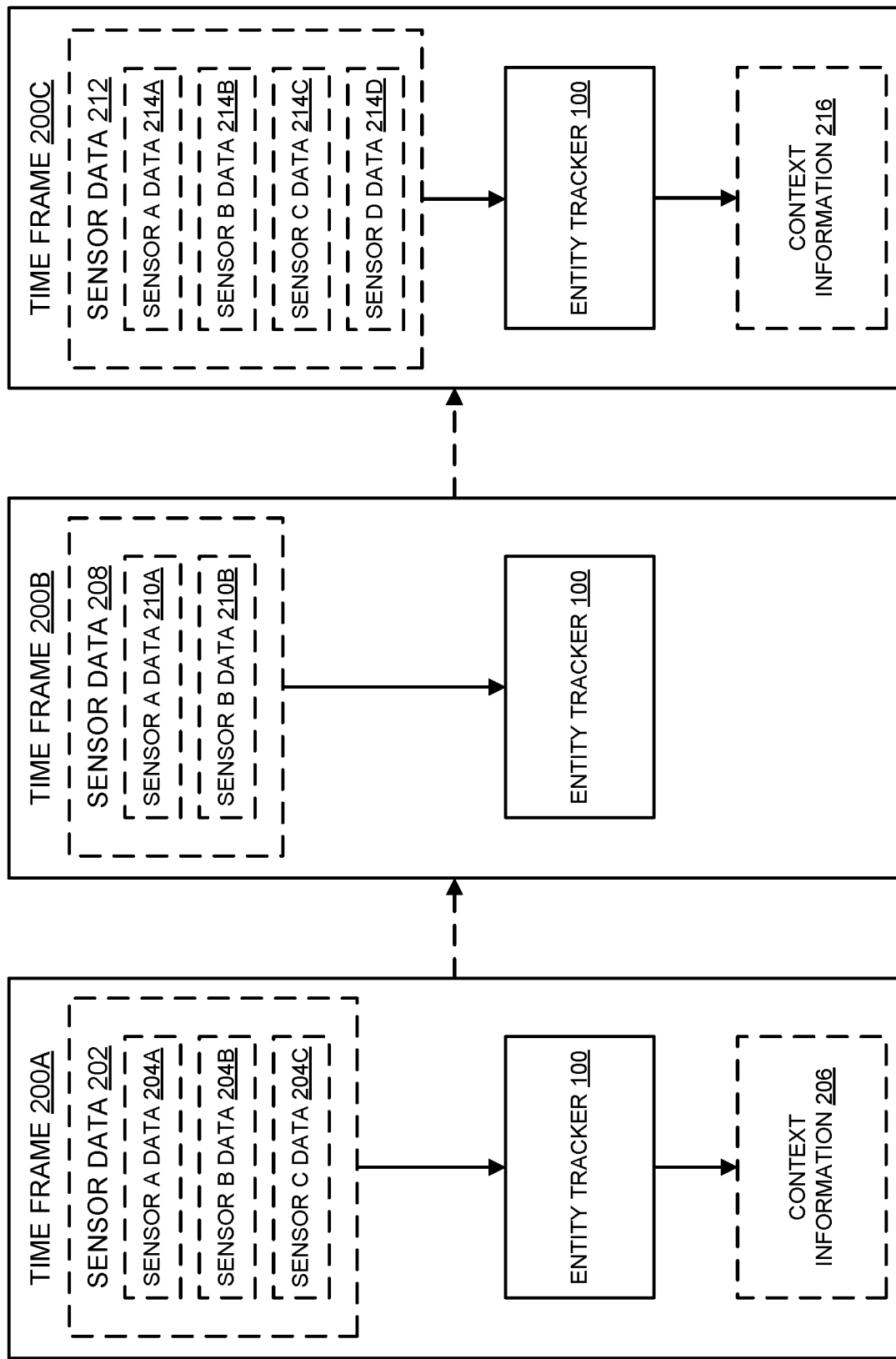
FIG. 4 schematically shows an entity-tracking computing system receiving and interpreting sensor data over multiple time frames according to examples of the present disclosure.

With reference now to FIG. 4, in some examples, individual sensors used with the entity-tracking computing system 100 may output data with a different frequency than other sensors used with the entity-tracking computing system. Similarly, sensors used with the entity-tracking computing system 100 may output data with a different frequency than the frequency with which the entity-tracking computing system evaluates the data and outputs context information. In the example of FIG. 4, entity-tracking computing system 100 may receive and interpret sensor data over multiple time frames 200A, 200B, and 200C. A single time frame may represent any suitable length of time, such as $\frac{1}{30}^{th}$ sec., $\frac{1}{60}^{th}$ sec., etc.

In this example, during time frame 200A entity-tracking computing system 100 receives a set of sensor data 202 including sensor A data 204A, sensor B data 204B, and sensor C data 204C. Such sensor data is interpreted by entity-tracking computing system 100 and transformed into context information 206, which may be used to determine an identity, position, and/or status of one or more detected entities as described above. During time frame 200B, entity-tracking computing system 100 receives sensor data 208, including sensor A data 210A and sensor B data 210B. Entity-tracking computing system 100 does not receive data from sensor C during time frame 200B, as sensor C outputs data at a different frequency than sensors A and B. Similarly, entity-tracking computing system 100 does not output context information during time frame 200B, as the entity-tracking computing system outputs context information at a different frequency than sensors A and B.

During time frame 200C, entity-tracking computing system 100 receives sensor data 212, including sensor A data 214A, sensor B data 214B, sensor C data 214C, and sensor D data 214D. Entity-tracking computing system 100 also outputs context information 216 during time frame 200C, which may be based on any or all of the sensor data received by the entity-tracking computing system since context information was last output in time frame 200A. In other words, context information 216 may be based at least in part on sensor data 208 as well as sensor data 212. In some examples, context information 216 may be based at least in part on sensor data 202 and sensor data 208, as well as sensor data 212.

As shown in FIG. 4, after the entity-tracking computing system 100 receives data from a particular sensor, multiple time frames may pass before the entity-tracking computing system receives more data from the same sensor. During these multiple time frames, entity-tracking computing system 100 may output context information. Similarly, the usefulness of data received from a particular sensor may vary from time frame to time frame. For example, at a first time frame the entity-tracking computing system 100 may receive audio data of a particular person speaking via a microphone, and accordingly identify an entity position 114 of the person with a relatively high confidence value. In subsequent time frames, the person may remain at the identified position, but also may have stopped speaking since the first time frame. In this case, the absence of useful data from the microphone may not be a reliable indicator of the absence of the person. Similar issues can arise with other types of sensors. For example, a camera may lose track of a person if he covers his face, or is occluded by an obstacle, such as another person or a moving object. In this case, though current camera data may not suggest the presence of the person, prior instances of camera data may suggest that the person is still located at the previously identified position. In general, while sensor data may reliably indicate the presence of an entity, such data may be less reliable in suggesting the absence of an entity.

Accordingly, the entity-tracking computing system 100 may utilize one or more confidence decay functions, which in different examples may be defined by the entity-tracking computing system and/or by the sensors themselves. A confidence decay function may be applied to sensor data to reduce the entity-tracking computing system's confidence in the data from a particular sensor as time passes since that sensor last positively detected an entity. As an example, after a sensor detects an entity at a particular location, the entity-tracking computing system 100 may report context information 110 indicating that the entity is at the location with relatively high confidence. If after one or more time frames the sensor no longer detects the entity at the location, and unless it subsequently gathers contradictory evidence, the entity-tracking computing system 100 still may report that the entity is at the location, though with a somewhat lower confidence. As time continues to pass since the sensor last detected the entity at the location, it becomes progressively less likely that the entity is still at the location. Accordingly, the entity-tracking computing system 100 may utilize the confidence decay function to progressively decrease the confidence value of its reported context information 110, eventually reaching 0% confidence if no additional sensors detect the entity.

In some cases, different confidence decay functions may be utilized with different sensors and sensor types. A selection of a particular decay function may depend at least in part on particular properties of a sensor. For example, confidence values associated with data from a video camera may decay more rapidly than confidence values associated with data from a microphone, as absence of an entity in a video frame is a more reliable indicator of the entity's absence than silence recorded by a microphone.

Figure 5:
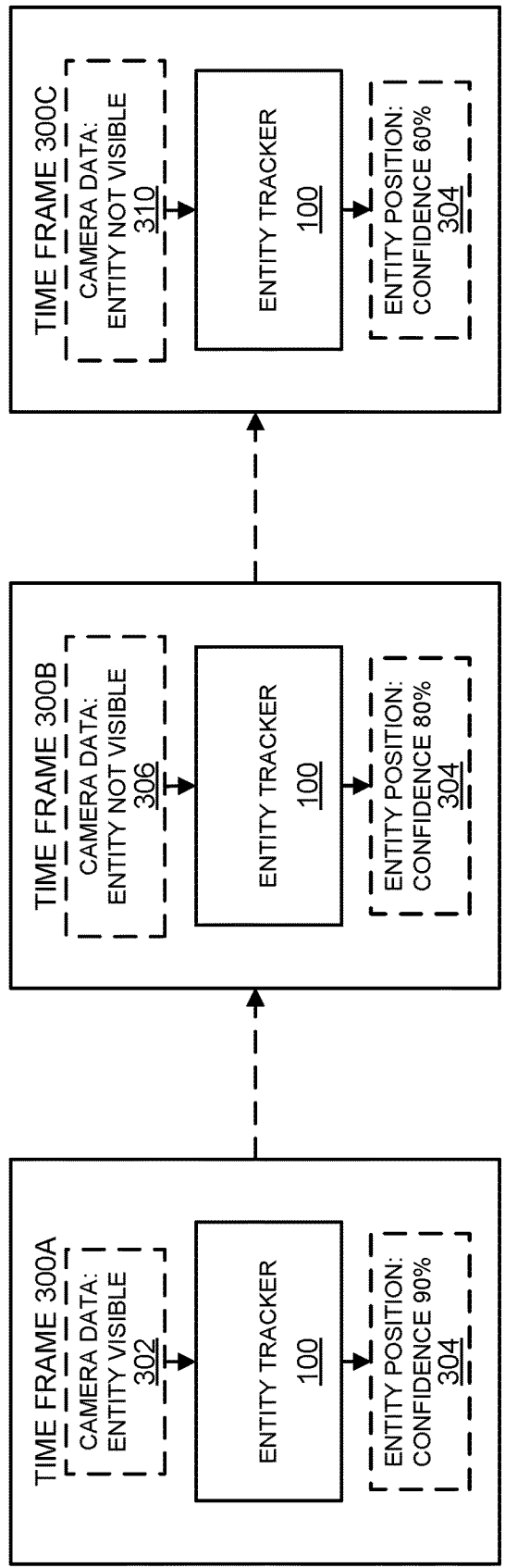
FIG. 5 schematically shows an example of sensor confidence decay over time via an entity-tracking computing system according to an example of the present disclosure.

One example of sensor confidence decay is schematically illustrated in FIG. 5, which shows entity-tracking computing system 100 receiving sensor data during three different time frames 300A, 300B, and 300C. During time frame 300A, entity-tracking computing system 100 receives camera data 302 in which an entity is visible in the frame. Based on this data, the entity-tracking computing system 100 reports the entity position 304 with a 90% confidence value. In time frame 300B, entity-tracking computing system 100 receives camera data 306 in which the entity is no longer visible in the frame. However, it is possible that the entity has not moved, and has merely become occluded, or otherwise undetectable to the camera. Accordingly, entity-tracking computing system 100 reports the same entity position 304, but with a lower confidence value of 80%.

Finally, in time frame 300C entity-tracking computing system 100 receives camera data 310 indicating that the entity is still not visible in the frame. As time has passed, it has grown less likely that the entity is still in the same position. Accordingly, the entity-tracking computing system 100 reports the same entity position 304 with a still lower confidence value of 60%.

In some examples, variable reliability of sensor data may be at least partially addressed by making use of data filtering techniques. In some examples, a Kalman filter may be utilized to filter sensor data. A Kalman filter is a mathematical function that may combine multiple uncertain measurements and output a prediction with more confidence than would be possible using any individual measurement. Each measurement input to the Kalman filter is given a weight based on the measurement's perceived reliability. Kalman filters operate in a two-step process, including a prediction step and an update step. During the prediction step, the filter outputs a prediction based on recent weighted measurements. During the update step, the filter compares its prediction to an actual observed value or state, and dynamically adjusts the weighting applied to each measurement so as to output more accurate predictions.

In some examples, entity-tracking computing system 100 may comprise a Kalman filter that combines data from a variety of sensors to compensate for lower sensor reliability, such as when sensor confidence values have decayed over time since the last positive detection. In some examples, entity-tracking computing system 100 may apply a Kalman filter to sensor data when one or more sensor confidence values are below a predetermined threshold. In an example scenario, image data from a camera may be analyzed using face detection techniques to reliably detect a person in a particular room. In response, the entity-tracking computing system 100 may report with high confidence that the person is located in the room.

In subsequent time frames, the camera may no longer be able to capture and/or positively recognize the person's face in the room. For example, the person's face may become occluded, or the camera may transmit data with a much lower frequency than the entity-tracking computing system 100 outputs context information 110. If the entity-tracking computing system 100 relied exclusively on data from the camera, then the confidence value of its reported position of the person would gradually decrease until the next positive detection. However and in some examples, data from the camera may be supplemented with data from other sensors. For example, during the subsequent time frames a microphone may report that it hears the person's voice in the room, or another sensor may report that it can detect the presence of the person's portable computing device in the room. In such cases, this data may be assigned weights by the Kalman filter, and may be used to predict the person's current location with more confidence than would be possible if only the camera data were used.

In some cases, detection of people and/or other entities in an environment can become more complicated when sensor data is contaminated by background information. Such background information may compromise the confidence with which the entity-tracking computing system 100 reports entity identity 112, position 114, and/or status 116. For example, the smart assistant device 20 may need to determine the identity of a person who is speaking in order to appropriately respond to a query or command. Such a determination can be difficult when multiple people are speaking at the same time, a television is playing, loud machinery is operating, etc.

Accordingly, the entity-tracking computing system 100 may use a variety of audio processing techniques to more confidently identify a particular active participant who is engaged in a conversation with other people and/or with the smart assistant device 20. As an example, the entity-tracking computing system 100 may implement a voice activity detection (VAD) engine that may distinguish human voices from environmental noise, and identify the presence or absence of human speech.

General-purpose VAD engines may be used for the purpose of classifying a particular segment of audio as including either speech or non-speech, with a corresponding confidence value. An entity-tracking computing system 100 also may utilize a speaker recognition engine to match a particular audio segment with a particular person. As more speech is received, the speaker recognition engine may be progressively tailored to classify the audio as including speech from a particular conversation participant, or not including speech from the particular conversation participant. In this manner, the entity-tracking computing system 100 may recognize speech from one or more particular persons/conversation participants.

Training of a speaker recognition engine may occur any time the entity-tracking computing system 100 has confidently identified a particular person and recorded audio that can be confidently attributed to that person. For example, using camera data, the entity-tracking computing system 100 may identify a particular person and determine that the person's lips are moving. The entity-tracking computing system 100 may simultaneously receive audio from a microphone that can be safely assumed to include speech from the identified person. Accordingly, the received audio can be used to retrain the speaker recognition engine to more specifically recognize the identified person's voice.

In some cases, such retraining may occur only when the person has been identified with a high confidence value (e.g., via accurate facial recognition or any other method), such as a confidence value exceeding a predetermined threshold, and when the entity-tracking computing system 100 has received an audio recording of the person's voice having high volume/amplitude and a high signal-to-noise ratio (S/N). Using this technique, the entity-tracking computing system 100 may accumulate a variety of person-specific voice models, allowing the entity-tracking computing system to more consistently identify speech from particular people and ignore background noise.

Figure 6:
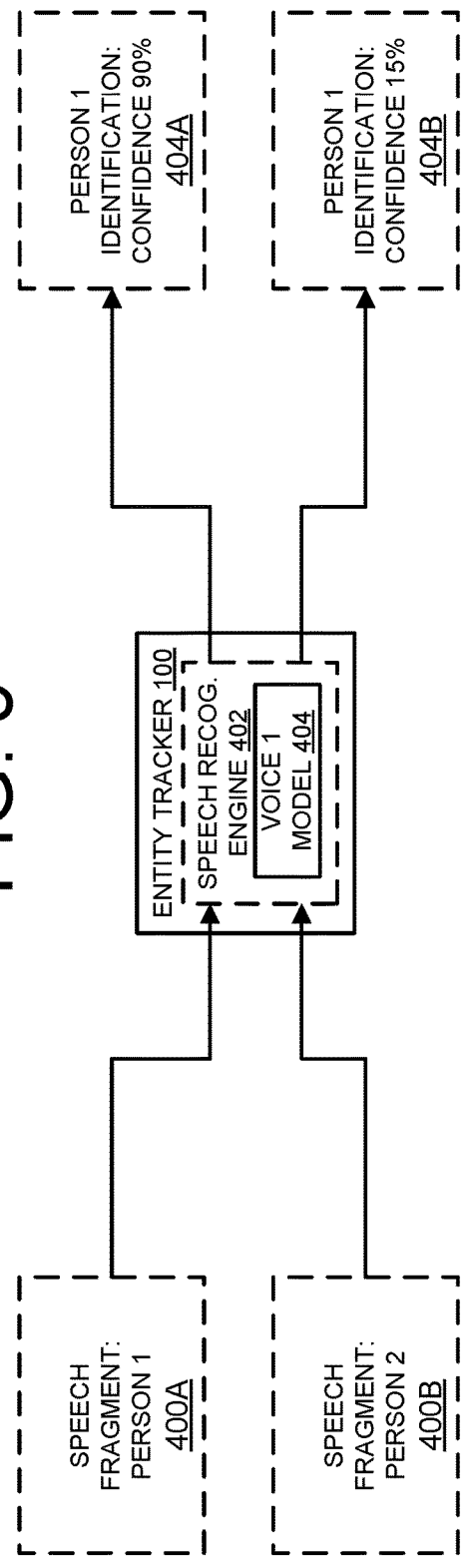
FIG. 6 schematically shows an example of using a trained voice recognition engine to recognize a person's speech according to examples of the present disclosure.

With reference now to FIG. 6, an example of using a trained speech recognition engine to recognize speech from a particular person is schematically illustrated. In this example, entity-tracking computing system 100 receives two speech fragments 400A and 400B. Speech fragment 400A includes recorded speech of a person 1, and speech fragment 400B includes recorded speech of a person 2. Entity-tracking computing system 100 includes a speech recognition engine 402 that has been specifically trained to recognize speech from person 1 using a voice 1 model 404, as described above. Voice 1 model 404 may be applied to each of speech fragment 400A and speech fragment 400B as they are received by the entity-tracking computing system 100.

Upon processing the speech fragments, the entity-tracking computing system 100 outputs a prediction of the likelihood that each speech fragment corresponds to person 1. As shown, for speech fragment 400A, the entity-tracking computing system outputs a person 1 identification 404A with a 90% confidence value, indicating that the speech fragment likely includes speech from person 1. For speech fragment 400B, the entity-tracking computing system outputs a person 1 identification 404B with a 15% confidence value, indicating that speech fragment 400B likely does not include speech from person 1.

In some examples, an entity-tracking computing system 100 may be configured to identify background noise present in an environment, and use audio processing techniques to subtract such background noise from received audio data. For example, a particular device in a person's home may be playing background audio, such as music or television/movie dialogue. Various microphone-equipped devices in the person's home may record such audio. Where such microphone-equipped devices include the smart assistant device 20 and/or provide audio data to the entity-tracking computing system 100, such background audio may compromise the ability of the system to identify, interpret and/or respond to human questions or commands.

Accordingly and in some examples, the device playing the background audio and/or another microphone-equipped device recording the background audio may send the captured audio signal to the entity-tracking computing system 100. In this manner, the entity-tracking computing system 100 may subtract the background audio from the audio signal received from the microphone-equipped devices. In some examples, the subtraction of the background audio signal from the recorded audio data may be performed by the device(s) that capture the audio data, or by associated audio-processing components, prior to sending the audio data to the entity-tracking computing system 100.

Additionally or alternatively, devices and/or the entity-tracking computing system 100 may be trained to recognize particular sources of background noise (e.g., from an air vent or refrigerator), and automatically ignore waveforms corresponding to such noise in recorded audio. In some examples, an entity-tracking computing system 100 may include one or more audio-recognition models trained specifically to recognize background noise. For example, audio from various noise databases may be run through supervised or unsupervised learning algorithms in order to more consistently recognize such noise. By allowing the entity-tracking computing system 100 to recognize irrelevant background noise, the ability of the entity-tracking computing system to recognize relevant human speech and other sounds may be improved. In some implementations, positional knowledge of a sound source may be used to focus listening from a directional microphone array.

As indicated above, in some cases an entity-tracking computing system as described herein may be configured to track entity positions as entities move throughout an environment. This may be done, for example, by interpreting data received from a plurality of sensors communicatively coupled to the entity-tracking computing system. However, such tracking can be complicated by the fact that sensors often have limited fields-of-detection (FODs), outside of which they cannot detect entity presence. Accordingly, if an entity moves outside the FOD of one sensor and enters the FOD of another sensor, the entity-tracking computing system may be unaware that it has detected the same entity twice, and accordingly conclude that two different entities are present. Similar problems can arise when, for example, two different sensors have overlapping FODs, an entity has a position within the overlap, and is detected by both sensors at once.

These problems are further complicated when hardware and/or FOD limitations prevent sensors from positively identifying an entity. For example, the entity-tracking computing device may be unable to positively identify an entity based on data from a relatively low-resolution camera, even after data from a different, higher resolution camera was used to successfully identify the same entity in a different location. Accordingly, the entity-tracking computing device may erroneously conclude that two entities are present.

Figure 7:
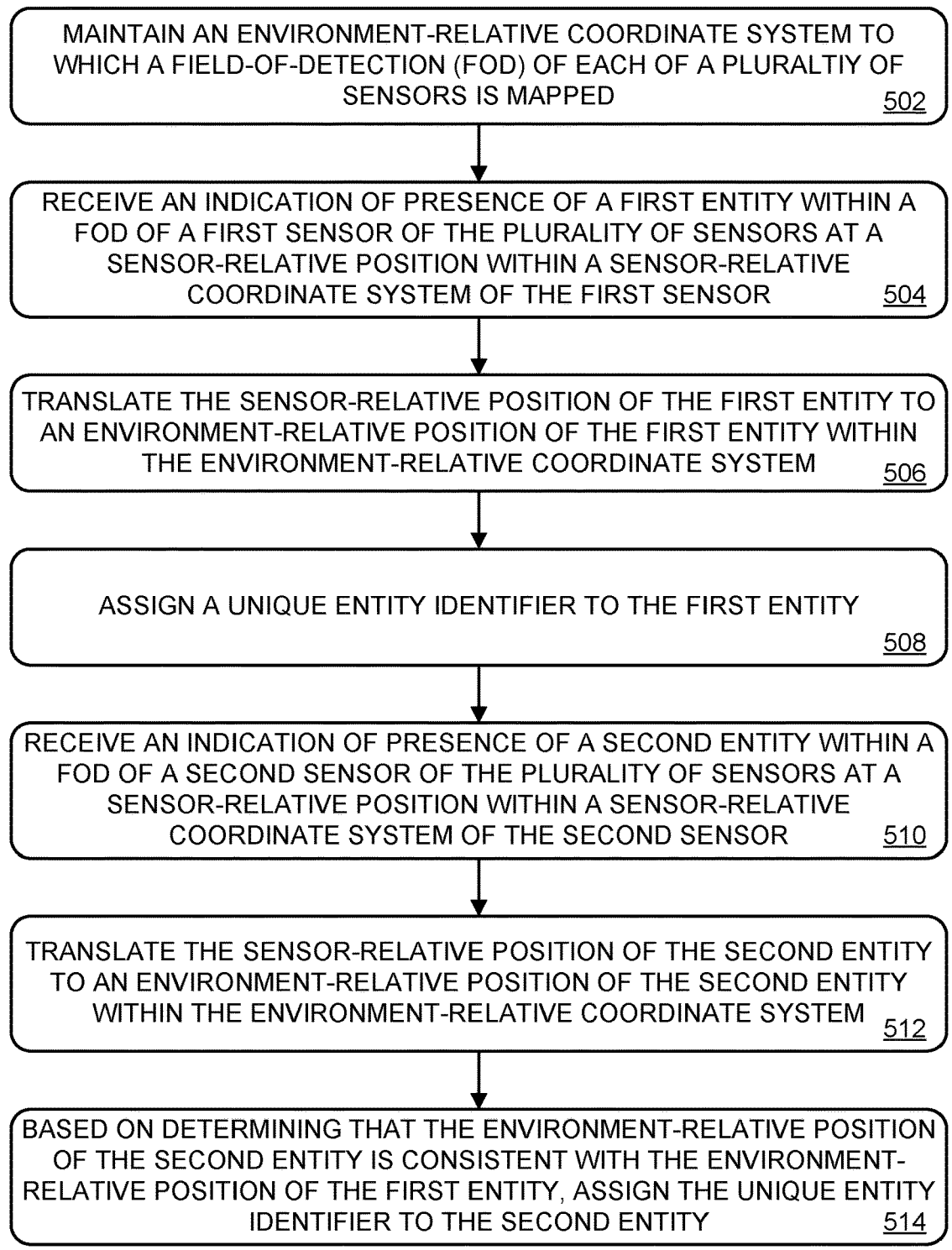
FIG. 7 illustrates an example method for tracking entities in an environment.

FIG. 7 therefore illustrates an example method 500 for tracking entities in an environment that at least partially alleviates the problems described above. Method 500 may be performed by smart assistant device 10, entity-tracking computing system 100, all-in-one computing device 160 of FIG. 15, remote service 170 of FIG. 17, and/or computing system 1300 of FIG. 18, as examples. An "environment" as used herein may refer to any real-world area, such as a single room, house, apartment, store, office, building, venue, outdoor space, grid sector, etc.

Figure 8A:
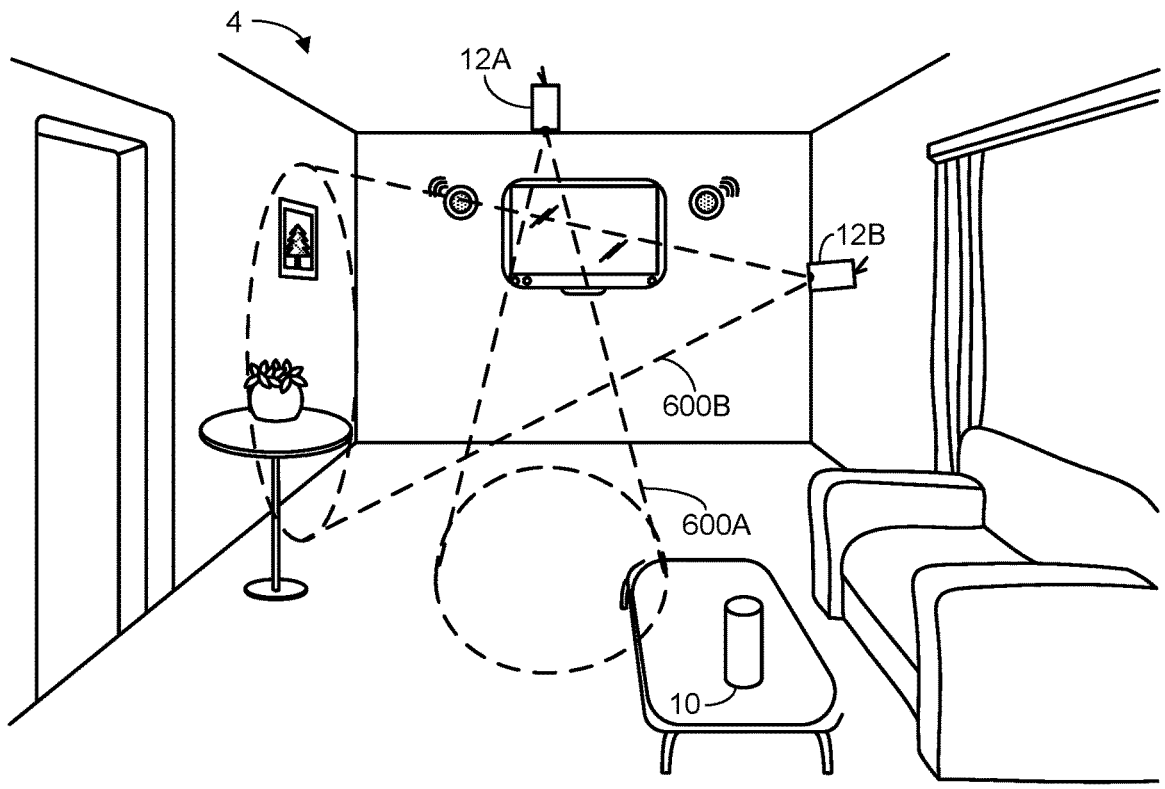
FIGS. 8A and 8B schematically illustrate fields-of-detection (FODs) of sensors in an environment.

At 502, method 500 includes maintaining an environment-relative coordinate system to which a FOD of each of a plurality of sensors is mapped. This is schematically illustrated in FIGS. 8A and 8B, which again show environment 4 of FIG. 1. As shown, sensor 12A has a FOD 600A, while sensor 12B has a FOD 600B. Because the sensors shown in FIG. 8A are cameras, FODs 600A and 600B are the fields-of-view (FOVs) of cameras 12A and 12B. In other words, FODs 600A and 600B show the portions of three-dimensional space in which cameras 12A and 12B can detect entities in environment 4. As will be described in more detail below, upon detecting an entity present in a FOD of a sensor (e.g., FOD 600A of camera 12A), the sensor may report this detection to an entity-tracking computing device such as, for example, smart assistant device 10.

Figure 8B:
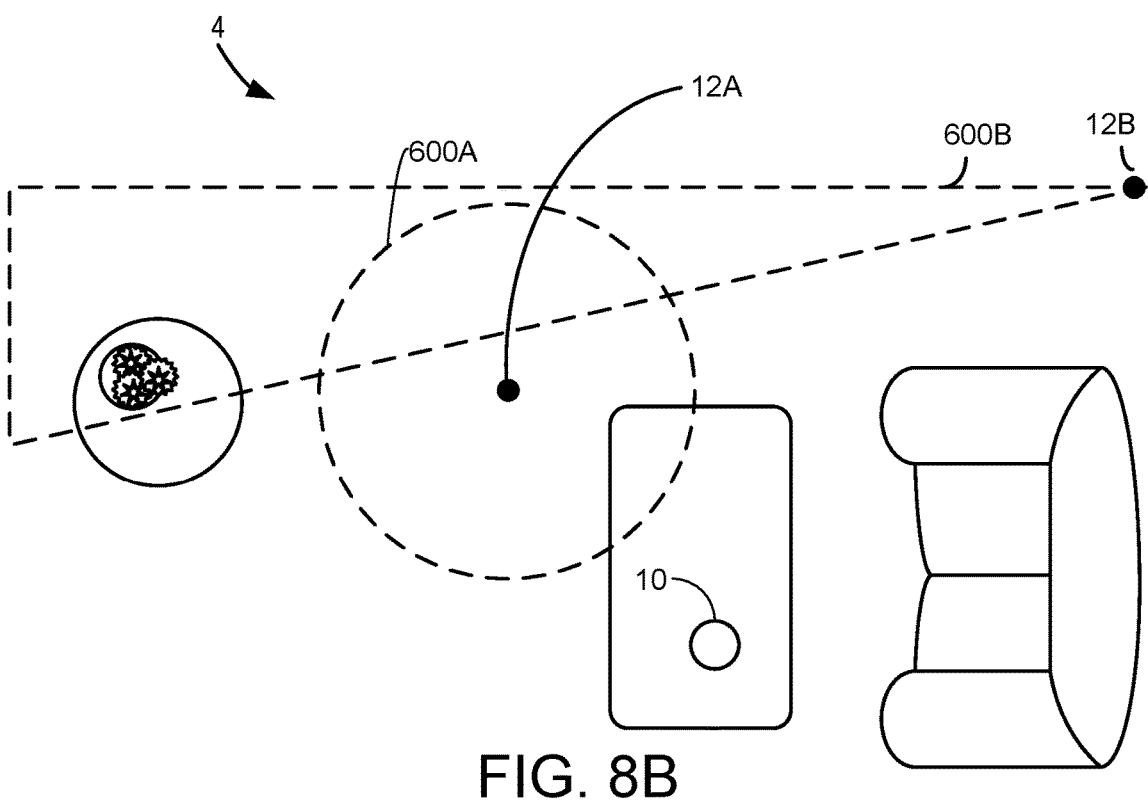

Though the sensors shown in FIGS. 8A and 8B are cameras, it will be understood that an entity-tracking computing device may be communicatively coupled to any of a variety of suitable sensors. As non-limiting examples, such sensors can include visible-light cameras, infrared (IR) cameras, depth cameras, cameras sensitive to other wavelengths of light, microphones, radar sensors, any of the other sensors described herein, and/or any other sensor useable to track an entity. Further, sensors communicating with the entity-tracking computing device can assume any suitable orientation. For example, cameras can be horizontally-oriented (e.g., to recognize human faces) and/or positioned overhead. Further, while FIG. 8A shows smart assistant device 10 being physically present in environment 4, it will be understood that this need not be the case. For example, an entity-tracking computing system may track entity positions in an environment while being physically located external to the environment (for example in another room, in another building, in a remote datacenter, etc.).

FIG. 8B shows an overhead view of environment 4 to illustrate that FODs 600A and 600B are partially overlapping. Because the FODs overlap, an entity (such as a human) located underneath camera 12A may be detected both by camera 12A and camera 12B. As indicated above, this can result in smart assistant device 10 concluding that two different entities are in environment 4, when in fact only one entity is present. This can be further complicated given the overhead position of camera 12A, which may prevent the entity-tracking computing system from facially-recognizing human entities based on data received from camera 12A.

Accordingly, as indicated above, an entity-tracking computing device may maintain an environment-relative coordinate system to which the FODs of sensors in the environment are mapped. This coordinate system may, for example, represent the entity-tracking computing system's understanding of the real-world relationships of FODs in the environment. In other words, the FOD of each sensor in the environment may be mapped to the environment-relative coordinate system, such that the smart assistant device has an understanding of the real-world areas in which the various sensors can detect entity presence. The environment-relative coordinate system may additionally include other information pertaining to the environment, such as the physical dimensions of the environment (e.g., the size of a room, building, outdoor space, grid sector), and/or the positions of any furniture, obstacles, doorways, sensors, or other detectable features present within the environment.

It will be understood that the environment-relative coordinate system may take any suitable form, and include any suitable information pertaining to an environment. The environment-relative coordinate system may utilize any suitable scale, grid system, and/or other method for mapping/quantifying an environment, and may use any suitable number of coordinates and parameters to define sensor FOD locations. In some cases, the environment-relative coordinate system may be a two-dimensional coordinate system and define sensor FODs relative to a two-dimensional surface, such as the floor of an environment. In other cases, the environment-relative coordinate system may define sensor FODs in three-dimensional space.

Figure 9:
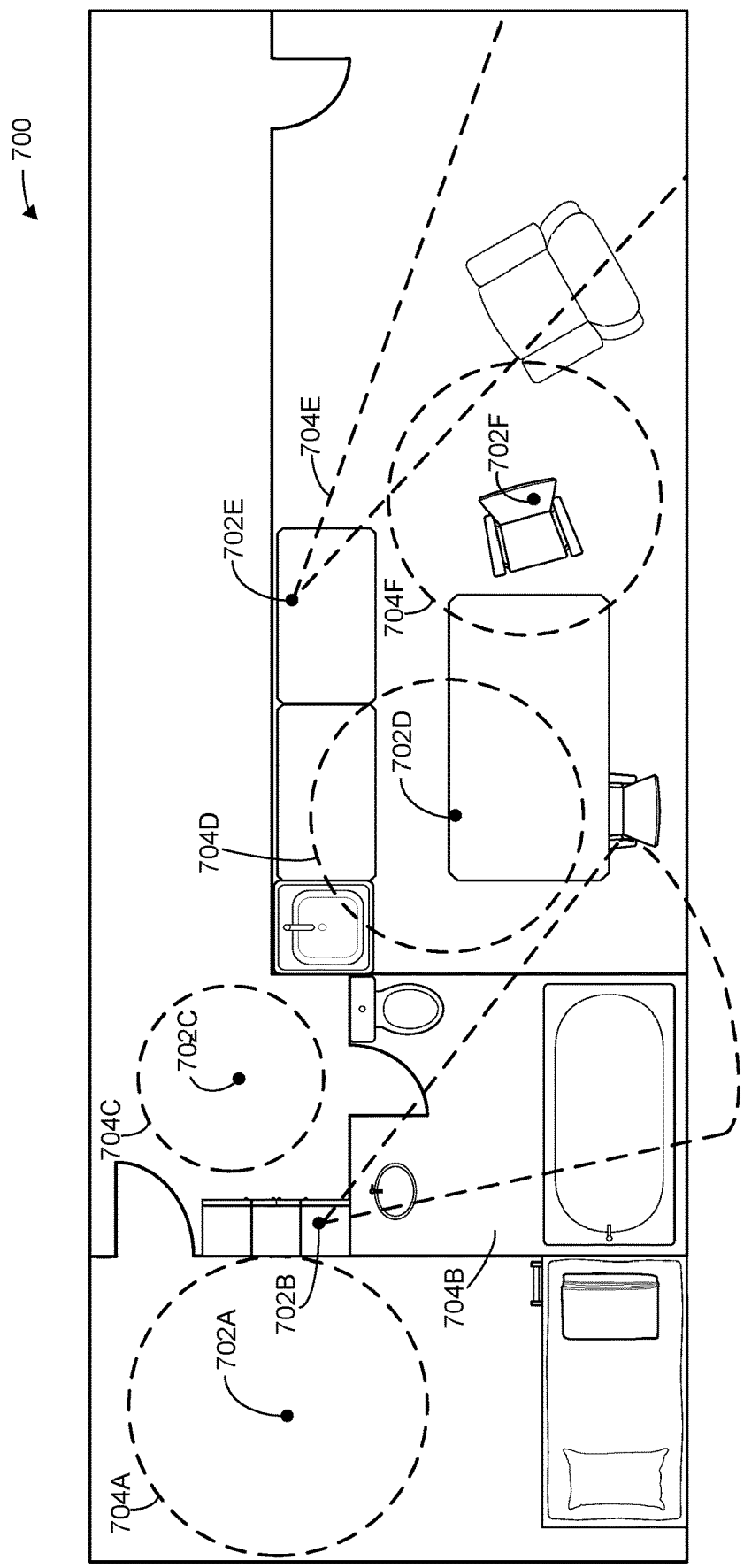
FIG. 9 schematically illustrates FODs of a plurality of different sensors in an environment.

Though FIGS. 8A and 8B focus on an environment consisting of only a single room, and including only two sensors, it will be understood that the entity tracking techniques described herein can be applied to environments of any size and including any number of sensors. As an example, FIG. 9 shows an overhead view of a different environment 700 including a plurality of sensors 702. As shown, environment 700 has multiple rooms, with sensors 702A-702F distributed throughout the multiple rooms. Multiple types of sensors are represented in FIG. 9, with sensors 702A, 702C, 702D, and 702F taking the form of overhead cameras, sensor 702E taking the form of a horizontally-facing camera, and 702B taking the form of a radar sensor.

Notably, radar sensors, such as sensor 702B, may have some ability to detect entities through obstructions such as walls, though may also lack sufficient resolution for consistently identifying the detected entities. Accordingly, radar sensors may in some cases be used to track entities that have been previously identified based data received from other sensors.

Tracking of entities through private environments, such as living spaces, bedrooms, bathrooms, etc., can present potential privacy concerns. Accordingly, all data collected by the entity-tracking computing system that may be personal in nature, such as entity positions, appearances, movements, behaviors, communications, etc., will be treated with the utmost respect for entity privacy. In some cases, any or all of the entity tracking techniques described herein may only be performed in response to receiving explicit user permission. For example, a user may specify which sensors are active, the amount and types of data collected by the sensors, which spaces or rooms in an environment are monitored by the entity-tracking computing system, a level of security or encryption to use with data collected by the entity-tracking computing system, whether collected data is stored locally or remotely, etc. In some examples, the user may choose to make use of relatively lower resolution sensors, such as radar sensors, for monitoring sensitive areas in an environment. This can alleviate at least some privacy concerns with regard to entity tracking, allowing the entity-tracking computing device to track entity movements without requiring users to install high-resolution cameras in sensitive areas, such as bathrooms.

Figure 10A:
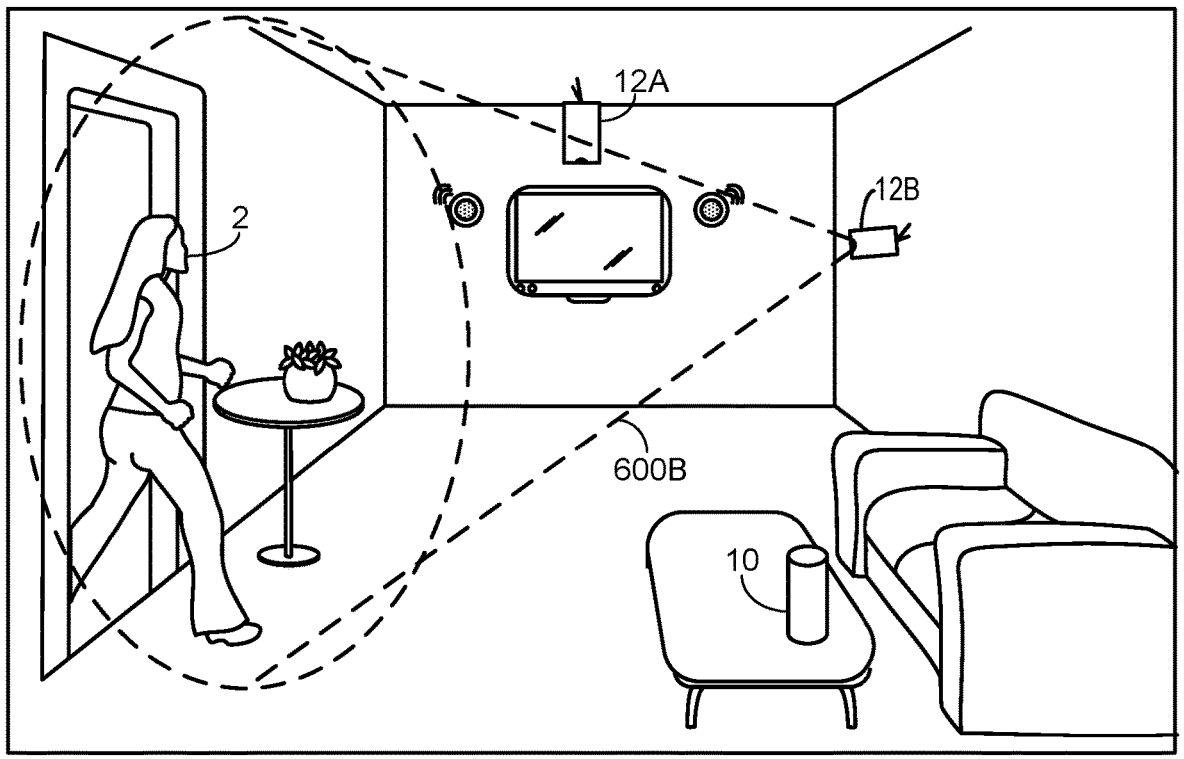
FIGS. 10A and 10B schematically illustrate detection of an entity in a FOD of a sensor.
Figure 10B:
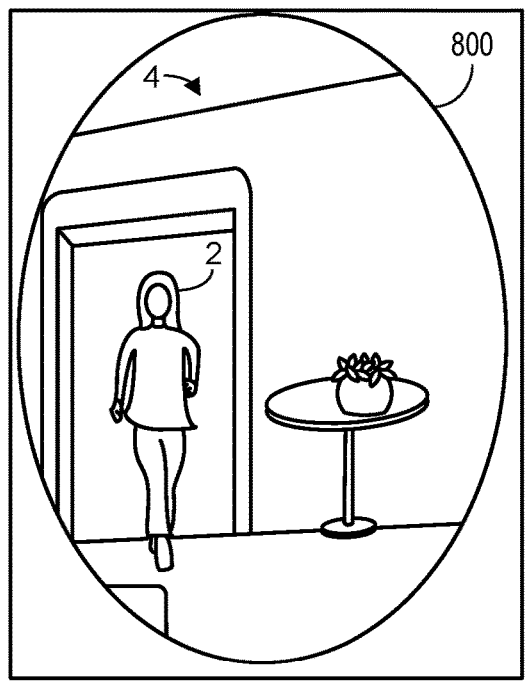

Returning briefly to FIG. 7, at 504, method 500 includes receiving an indication of presence of a first entity within a FOD of a first sensor at a sensor-relative position within a sensor-relative coordinate system of the first sensor. This is schematically illustrated in FIGS. 10A and 10B, which again show environment 4 of FIG. 1. Specifically, FIG. 10A shows human entity 2 entering FOD 600B of camera 12B, while FIG. 10B shows a view 800 of environment 4 from the perspective of camera 12B. In this example, the first sensor is camera 12B, and the first entity is human entity 2.

Upon detecting human entity 2 within FOD 600B, the camera may transmit an indication of presence of the detected entity to the entity-tracking computing device. The indication of entity presence may take any suitable form depending on the implementation and the specific sensors used. In an example scenario, a camera may capture an image of a human face. In some cases, the camera may transmit unprocessed image data to the entity-tracking computing system, the image data including one or more pixels corresponding to the face. The transmitted pixels corresponding to the entity therefore represent the indication of presence of the entity, and may be processed by the entity-tracking computing device to determine the position and/or identity of the entity. Notably, image data may be transmitted by the camera with any suitable frequency, and need not only be transmitted in response to detecting a candidate entity. In other cases, the camera may perform some degree of processing on the image data, and send a summary or interpretation of the data to the entity-tracking computing system. Such a summary may indicate, for example, that a specific, identified human is present at a specific position given by a sensor-relative coordinate system of the sensor. Regardless of the specific form taken by the indication of entity presence, in the example scenario, the data received by the entity-tracking computing device may still be useable to identify the human face detected in the FOD of the sensor.

The indication of entity presence can take other suitable forms depending on which sensor detects the entity. For example, when the sensor is a microphone, the indication of entity presence can include recorded audio of the entity's voice or a sensor-relative location of the entity determined via sound processing. When the sensor is a radar sensor, the indication of entity presence can include a silhouette or "blob" formed through detection of radio waves reflecting off the entity. It will be understood that different sensors will detect entity presence in different ways, and an indication of entity presence can take any suitable form depending on the specific sensor(s) used. Further, processing of sensor data may take place on the entity-tracking computing system, on the sensor or related components, and/or distributed among multiple devices or systems.

Along with the indication of entity presence, the entity-tracking computing device also may receive an indication of a sensor-relative position of the detected entity within a sensor-relative coordinate system. For example, when the sensor is a camera, the sensor-relative position may be given by a set of pixel coordinates relative to a two-dimensional grid of pixels captured by the camera. When the camera is a depth camera, the sensor-relative position of the entity may be a three-dimensional position. As with the indication of entity presence, the sensor-relative position of the entity can take any suitable form. For example, when the sensor is a microphone, the sensor-relative position may be inferred from an amplitude of the recorded audio signal, thereby serving as an indicator of the entity's distance from the sensor. Similarly, as with the environment-relative coordinate system, the sensor-relative coordinate system of each sensor may take any suitable form depending on the type of data collected or observed by the sensor, and may use any scale, grid system, or other suitable method for demarcating/quantifying a sensor's local environment.

Returning briefly to FIG. 7, at 506, method 500 includes translating the sensor-relative position of the first entity to an environment-relative position of the first entity within the environment-relative coordinate system. Such translation may rely on a mapping of the FOD of the sensor to the environment-relative coordinate system, as indicated above. This mapping may be achieved in any of a variety of suitable ways, and may be performed at any suitable time. For example, in some cases the mapping of sensor FODs to the environment-relative coordinate system may be done upon installation of sensors of the entity-tracking computing system, gradually developed as the entity-tracking computing system is used, and/or at another suitable time.

In some examples, mapping the FOD of a sensor to the environment-relative coordinate system includes resolving a position of a calibration device relative to the sensor, and identifying a correspondence between the position of the calibration device and the FOD of the sensor. Such a calibration device may take a variety of suitable forms. For example, in some cases the calibration device may include one or more internal position and/or motion sensors, such as cameras and image processing systems (e.g., utilizing optical flow and/or feature detection), accelerometers, gyroscopes, magnetometers, global positioning satellite (GPS) receivers, wireless network interfaces, etc., through which the calibration device can observe and track its own pose and movements through the environment. The position of the calibration device may be reported with any suitable specificity, such as a three degree-of-freedom (3 DOF) or six degree-of-freedom (6 DOF) pose. Because the calibration device will generally be portable, it may be implemented in a hand-held form factor, wearable form factor, and/or any other suitable form factor that permits movement of the calibration device throughout the environment. Data from the calibration device may be received by the entity-tracking computing system or a separate coordinate calibration computer, which can in turn use such data to build or maintain the environment-relative coordinate system, and/or otherwise establish the position of the calibration device within the environment-relative coordinate system. In other words, resolving the position of the calibration device includes receiving from the calibration device information useable to assess the position of the calibration device within the environment-relative coordinate system.

To determine the position and extent of the FOD of a sensor within the environment-relative coordinate system, the entity-tracking computing system may identify correspondences between the position of the calibration device and the FOD of the sensor. In some examples, this may include receiving, from the sensor, information useable to assess a position of the calibration device within a sensor-relative coordinate system of the sensor. In other words, based on the calibration device entering the FOD of the sensor, data recorded by the sensor may be used to determine the position of the calibration device relative to the sensor. This may be done, as an example, by visually recognizing presence of the calibration device in a camera feed. Accordingly, during mapping of sensor FODs to the environment-relative coordinate system, a human user may move the calibration device throughout an environment, such that the calibration device is present at some point in time within each FOD to be mapped. This may include the calibration device and/or entity-tracking computing system providing instructions to the human user for moving the calibration device along a preprogrammed route, and/or performing one or more calibration movements. In other examples, calibration need not require human intervention. For example, the calibration device may be implemented as a robot capable of self-directed movement.

In some cases, the calibration device may incorporate one or more positioning markers, the presence of which can be recognized in sensor data. Such positioning markers may be visually recognized, detected based on observing unique wireless signals emitted by the positioning markers, detected based on recording a unique sound produced by the positioning markers, etc. It will be understood that the calibration device may include any suitable number of positioning markers, which may in turn have any suitable size, shape, and orientation relative to the calibration device. In some implementations, a positioning marker may include a light configured to flash with an identifiable frequency. Different positioning markers can be instructed to flash with different frequencies, thus helping a system to distinguish between different positioning markers.

Figure 11A:
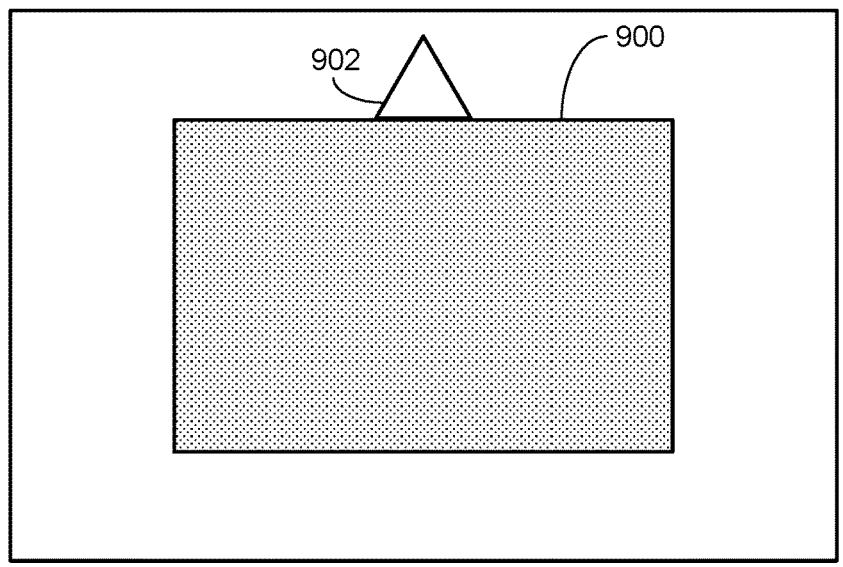
FIGS. 11A and 11B schematically illustrate resolving the position of a calibration device relative to a sensor.
Figure 11B:
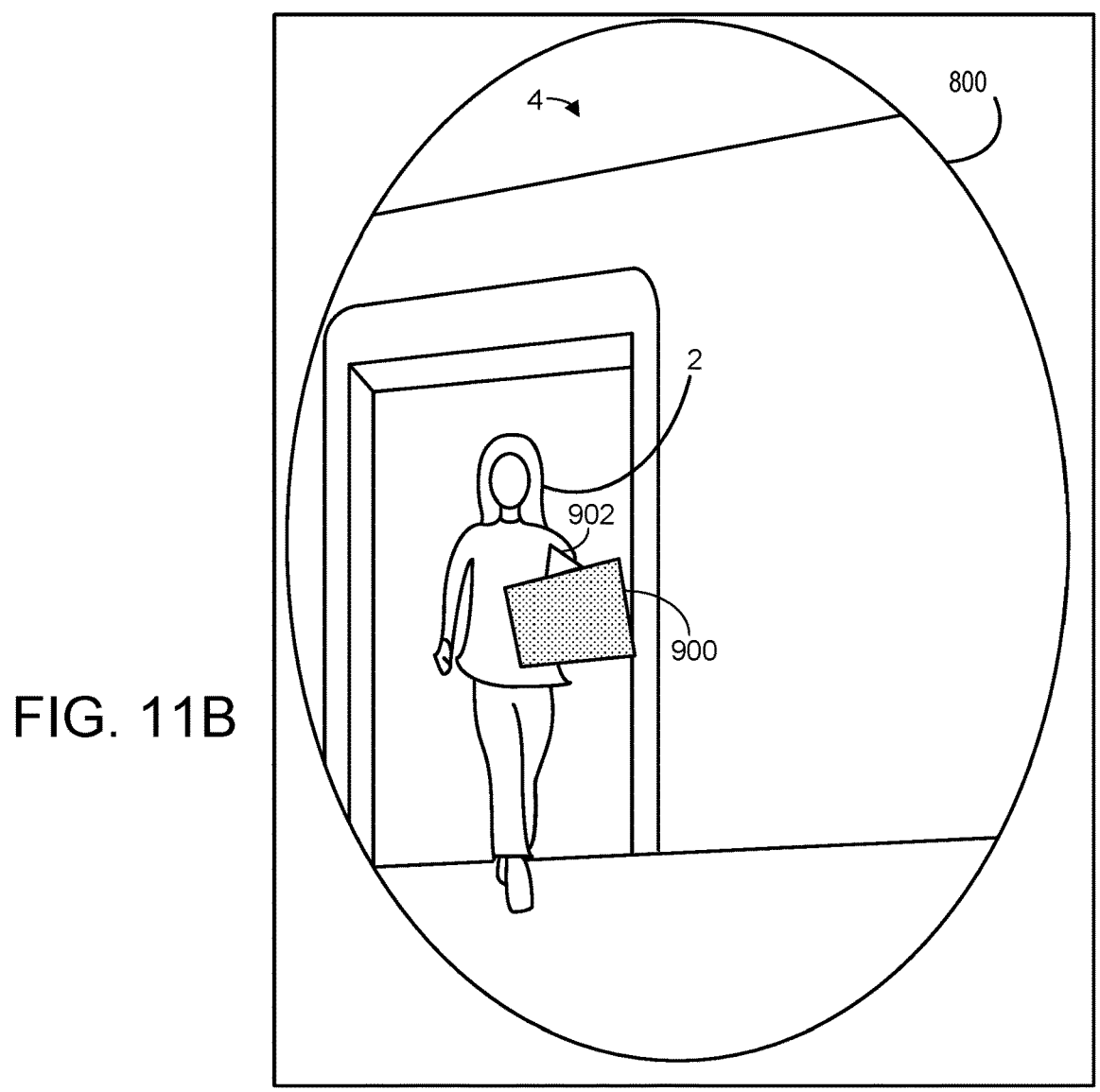

FIGS. 11A and 11B schematically illustrate an example approach for resolving the position of a calibration device. Specifically, FIG. 11A schematically shows an example calibration device 900 that includes a positioning marker 902, pictured as a triangle. In some cases, positioning markers may use distinctive shapes with known sizes. Accordingly, if a positioning marker is observed in image data recorded by a camera, the distance of the positioning marker away from the camera, as well as the orientation of the positioning marker relative to the camera, can be inferred by observing the apparent size and orientation of the positioning marker as imaged by the camera. Similarly, the calibration device can incorporate multiple positioning markers, with each positioning marker having a known size, shape, and spatial relationship with the other positioning markers. Accordingly, observing positioning marker sizes, shapes, and spatial relationships as recorded by sensors can enable the position of the calibration device to be determined.

This is illustrated in FIG. 11B, which again shows view 800 of camera 12B in environment 4. Within view 800, human entity 2 is visible holding calibration device 900. Based on observing the apparent size and orientation of positioning marker 902, camera 12B and/or the entity-tracking computing system may determine the position and orientation of the positioning marker, and therefore the calibration device, relative to the camera. In some cases, position and orientation of the calibration device may be mathematically resolved with positioning data received from the calibration device to determine the position of the FOD of the camera relative to the environment.

In other examples, resolving the position of the calibration device may be done in other suitable ways. As an example, the entity-tracking computing system may receive, from the calibration device, information useable to assess the position of a sensor within the environment-relative coordinate system. Accordingly, the sensor may incorporate one or more positioning markers, which may be similar to those described above with respect to the calibration device. The calibration device may detect the sensor-based positioning markers, and report the positions of the positioning markers along with the position of the calibration device itself, enabling the entity-tracking computing system to determine the environment-relative position of the sensor.

Figure 12:
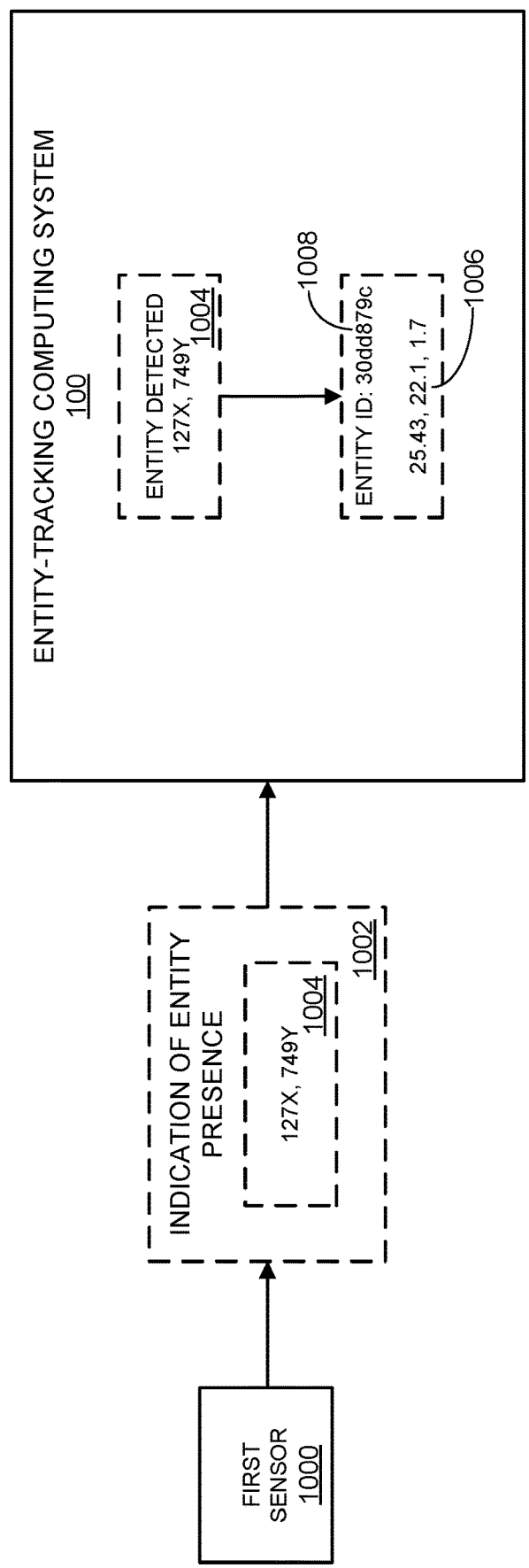
FIG. 12 schematically illustrates translating of a sensor-relative position of an entity to an environment-relative position.

Based on this mapping of sensor FODs to the environment-relative coordinate system, which again may be developed at any time, the entity-tracking computing system may translate sensor-relative positions of detected entities to environment-relative positions within the environment-relative coordinate system. This process is schematically illustrated in FIG. 12, which schematically shows an example first sensor 1000 that has detected presence of a first entity within its FOD. Accordingly, first sensor 1000 has transmitted an indication of entity presence 1002, including a sensor-relative position 1004 of the first entity within a sensor-relative coordinate system of sensor 1000. The indication of entity presence is received by entity-tracking computing system 100, which translates the sensor-relative position of the entity to an environment-relative position of the entity based on knowledge of the environment-relative position of the FOD of the sensor.

Returning briefly to FIG. 7, at 508, method 500 includes assigning a unique entity identifier to the first entity. The unique entity identifier may take any suitable form, and may depend on whether the detected entity is a known, previously identified entity. For example, in some cases the first entity may be unidentified, and accordingly may be assigned a generic identifier, allowing the entity-tracking computing system to distinguish the entity from other tracked entities in the environment. This is shown in FIG. 12, in which the detected first entity is assigned a unique entity identifier 1008.

In other examples, the sensor and/or entity-tracking computing system may determine that the entity is a previously-identified human, and accordingly assign a previously-assigned entity identifier associated with the previously-assigned human. The previously-assigned entity identifier may be, for example, a previously-assigned generic identifier, a name of the detected human, a user profile of the detected human, etc. As described above with respect to entity identifier 104, detected entities may be identified with any suitable specificity. Further, entities can be identified in any of a variety of suitable ways, potentially involving facial recognition, voice recognition, detecting presence of portable computing devices associated with known entities, evaluating human height, weight, body shape, gait, hairstyle and/or shoulder shape (e.g., from an overhead camera), etc.

Returning briefly to FIG. 7, at 510, method 500 includes receiving an indication of presence of a second entity within a FOD of the second sensor at a sensor-relative position within a sensor-relative coordinate system of the second sensor. This may occur as described above with respect to receiving the indication of presence of the first entity. Continuing with FIG. 7, at 512, method 500 includes translating the sensor-relative position of the second entity to an environment-relative position of the second entity within the environment-relative coordinate system. Again, this may be done as described above with respect to the first entity.

In some cases, the second entity may be a distinct individual from the first entity. However, as discussed above, in other cases the second entity may be the same as the first entity, though merely detected by a different sensor.

For example, the entity may be located at a position that falls within the FODs of two different sensors, causing both sensors to detect the entity. As another example, the first entity may move out of the FOD of the first sensor, and enter the FOD of the second sensor. Determining that the same entity has been detected by both sensors can be complicated by hardware limitations of one or both sensors. For example, in some scenarios, data received from the second sensor may not be sufficient to identify the second entity without the data received from the first sensor.

Accordingly, at 514, method 500 includes, based on determining that the environment-relative position of the second entity is consistent with the environment-relative position of the first entity, assigning the unique entity identifier to the second entity. This may be done in a variety of suitable ways. For example, determining that the environment-relative position of the second entity is consistent with the environment-relative position of the first entity may include determining that the environment-relative position of the second entity is within a threshold distance of the environment-relative position of the first entity. This may be the case, for example, when two different sensors have overlapping FODs, and the entity is located within the overlap. Accordingly, the entity may be detected by each sensor, and recorded by the entity-tracking computing device as two separate entities.

In some cases, upon detecting the first entity based on data from a first sensor, the entity-tracking computing system may be initially unable to identify the first entity. Accordingly, the entity-tracking computing system may track the first entity using a generic identifier assigned to the first tracked entity, so as to distinguish the first tracked entity from other tracked entities in the environment. At a later time, after a second sensor detects a second entity, the entity-tracking computing system may determine that the first tracked entity is in fact the same as the second entity. Further, based on sensor data collected by the second sensor, the entity-tracking computing system may identify the second entity, for example as a human that has been previously identified. The entity-tracking computing system may then record an association between the generic identifier and a user name or profile of the previously-identified human, and/or replace the generic identifier with a previously-assigned entity identifier associated with the previously-identified human. In this manner, the entity-tracking computing system may first track a detected entity, and tag the entity once additional sensor data is received.

In other cases, the first entity may be initially identified as a previously-identified human, based on data received from a first sensor. Accordingly, the entity-tracking computing system may tag the first entity with a unique entity identifier, for example by assigning to the entity a previously-assigned entity identifier associated with the previously-identified human, or by recording an association between a generic identifier assigned to the first entity and a user name or profile of the previously-identified human. At a later time, after a second sensor detects a second entity, the entity tracking computing system may determine that the first tagged entity and the second entity are in fact the same entity. The entity-tracking computing system may then tag the second entity with the unique entity identifier. In some examples, this may be done even when data received from the second sensor would be insufficient on its own to tag the second entity, for example due to hardware or FOD limitations of the second sensor. In this manner, the entity-tracking computing system is able to tag an entity, and continue to track the entity even when, for example, the first entity leaves a FOD of the first sensor.

In a specific example, a human face may be detected by a horizontally-facing IR camera, while an overhead human silhouette is detected by an overhead depth camera. Based on data received from the two cameras, the entity-tracking computing device may construct a vector from the horizontally-facing IR camera toward the observed human face within the environment-relative coordinate system. If the constructed vector intersects and/or passes within a threshold distance of the human silhouette observed by the overhead camera, the entity-tracking computing device may conclude that both sensors are detecting the same entity. As such, even after the entity leaves the FOD of the horizontally-facing IR camera, the entity may be tracked by the overhead depth camera. Furthermore, even though the overhead depth camera does not have a proper view for recognizing the face of the entity, the identification learned from the horizontally-facing IR camera can be applied to the entity while the entity is tracked out of the FOD of the horizontally-facing IR camera.

This process is schematically illustrated in FIGS. 13A-13D. Specifically, FIG. 13A shows an overhead view of environment 4 of FIG. 1, in which an entity E1 has entered FOD 600A of sensor 12A. Based on an indication of entity presence transmitted from sensor 12A to the entity-tracking computing device, the entity-tracking computing device records an environment-relative position and unique entity identifier for the entity, as shown in table 1100A of FIG. 13A.

In FIG. 13B, sensor 12B detects a second entity E2 within FOD 600B of sensor 12B. Accordingly, the entity-tracking computing system records an environment-relative position and unique entity identifier for the second entity in table 1100B of FIG. 13B. However, in reality, only one entity is present within environment 4. Because this entity is located at a position that falls within the FODs of both sensors 12A and 12B, each sensor has detected the entity, causing the entity-tracking computing device to make the initial inference that two entities are present.

In FIG. 13C, a threshold distance 1102 is shown centered on the position of the second entity. As discussed above, in some cases determining that the environment-relative position of the second entity is consistent with the environment-relative position of the first entity may include determining that the environment-relative position of the second entity is within a threshold distance of the environment-relative position of the first entity. As shown, the detected position of E1 falls within the threshold distance of E2.

Accordingly, in FIG. 13D, the entity-tracking computing system has concluded that the environment-relative position of the second entity is consistent with the environment-relative position of the first entity. Therefore, the entity-tracking computing system has assigned the unique entity identifier of the first entity to the second entity, and only one entity identifier and position is recorded in table 1100D of FIG. 13D.

The threshold distance may be a fixed distance, which may be selected based on the resolution(s) of the sensor(s). In some implementations, the threshold distance may be dynamically adjusted based on confidence of detection, number of detected entities, and/or other factors.

In another example scenario, upon being detected within the FOD of a first sensor, an entity may move outside of the FOD of the first sensor and, at some future time, enter the FOD of a second sensor. Accordingly, in some cases, the entity-tracking computing system may be configured to predict a path of the first entity after the first entity leaves the FOD of the first sensor, and determine that the environment-relative position of the second entity is consistent with the environment-relative position of the first entity upon determining that the environment-relative position of the second entity is consistent with the path after the second entity enters the FOD of the second sensor.

Figure 14A:
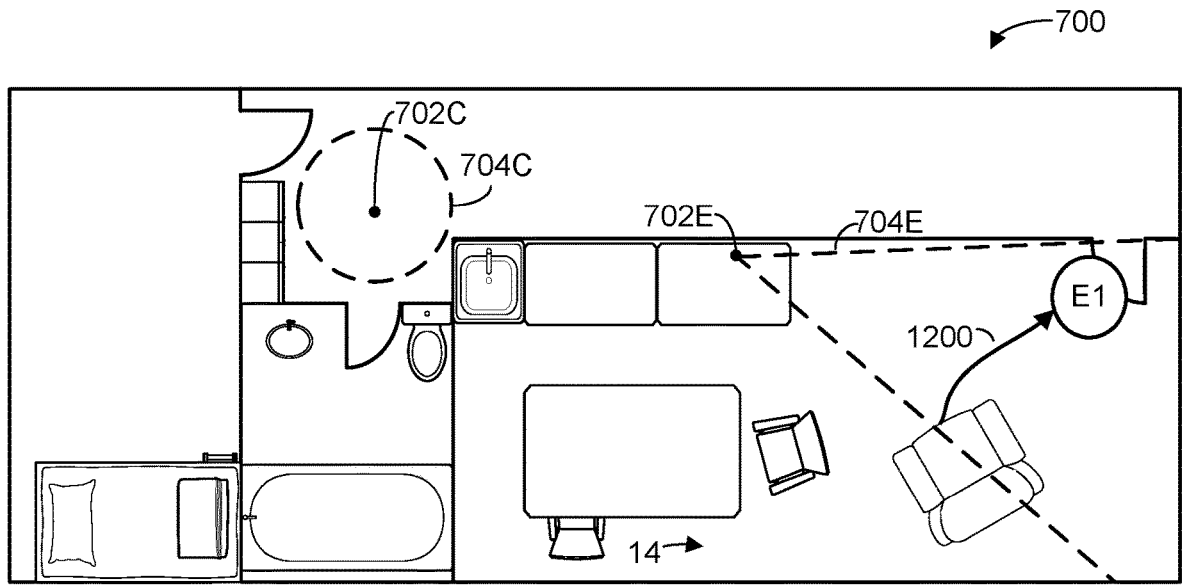
FIGS. 14A-14D schematically illustrate another example of determining that an environment-relative position of a second entity is consistent with an environment-relative position of a first entity.
Figure 14B:
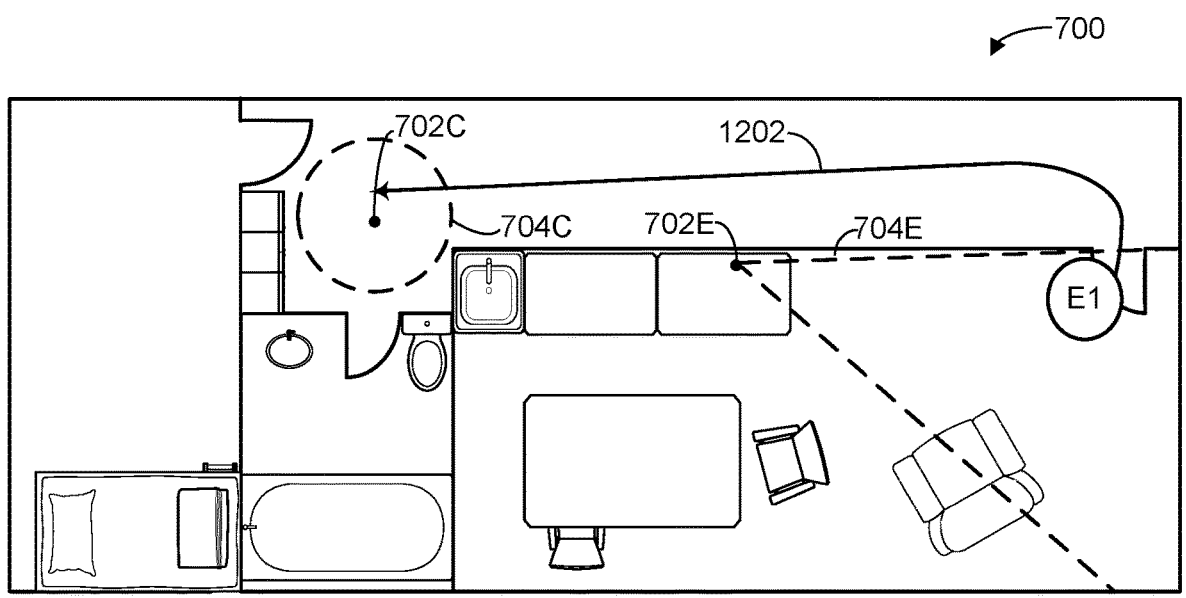

This process is schematically illustrated in FIGS. 14A-14D, which show an overhead view of environment 700 from FIG. 9. As shown, sensor 702E has detected presence of a first entity E1 within FOD 704E. Based on observed movements 1200 of the first entity (i.e., out the door into the hallway), the entity-tracking computing system may predict one or more potential paths of the first entity in which the first entity leaves the room (e.g., a path in which the user walks down the hallway). This is shown in FIG. 14B, showing the predicted path 1202 of the first entity away from FOD 704E and down the hallway toward FOD 704C.

An entity path predicted by an entity-tracking computing system may take any suitable form, and have any suitable specificity. For example, in some cases, predicting a path of an entity may include observing a direction and speed of the entity, and extrapolating this direction and speed into the future as a vector. However, in other cases, predicting an entity path may be inference-based. For example, in FIG. 14A, the first entity is observed to be moving out the door between the living room and the hallway. Because there are no doors in the hallway between the living room and the position of sensor 702C, the entity-tracking computing device may reasonably predict that the entity will walk down the hallway and eventually enter the FOD of sensor 702C. As another example, the entity-tracking computing device may observe over time that a human entity consistently goes to bed, leaves the house, etc., at approximately the same time every day. Accordingly, upon observing movement at the observed time, the entity-tracking computing system may predict that the human is, for example, going to bed.

Figure 14C:
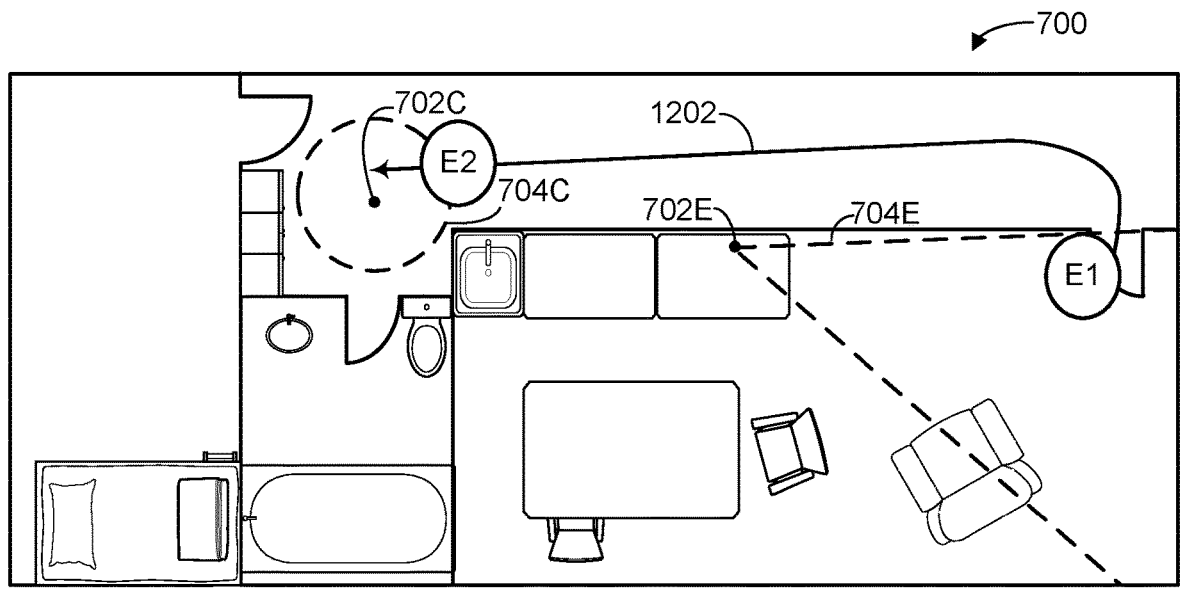

In FIG. 14C, the entity-tracking computing system has received an indication of presence of a second entity E2 within FOD 704C of sensor 702C. As discussed above, in some cases the entity-tracking computing device may determine that the environment-relative position of the second entity is consistent with the environment-relative position of the first entity upon determining that the environment-relative position of the second entity is consistent with a predicted path of the first entity after the second entity enters the FOD of the second sensor. Notably, in FIG. 14C, the position of second entity E2 is consistent with path 1202 predicted for first entity E1.

Figure 14D:
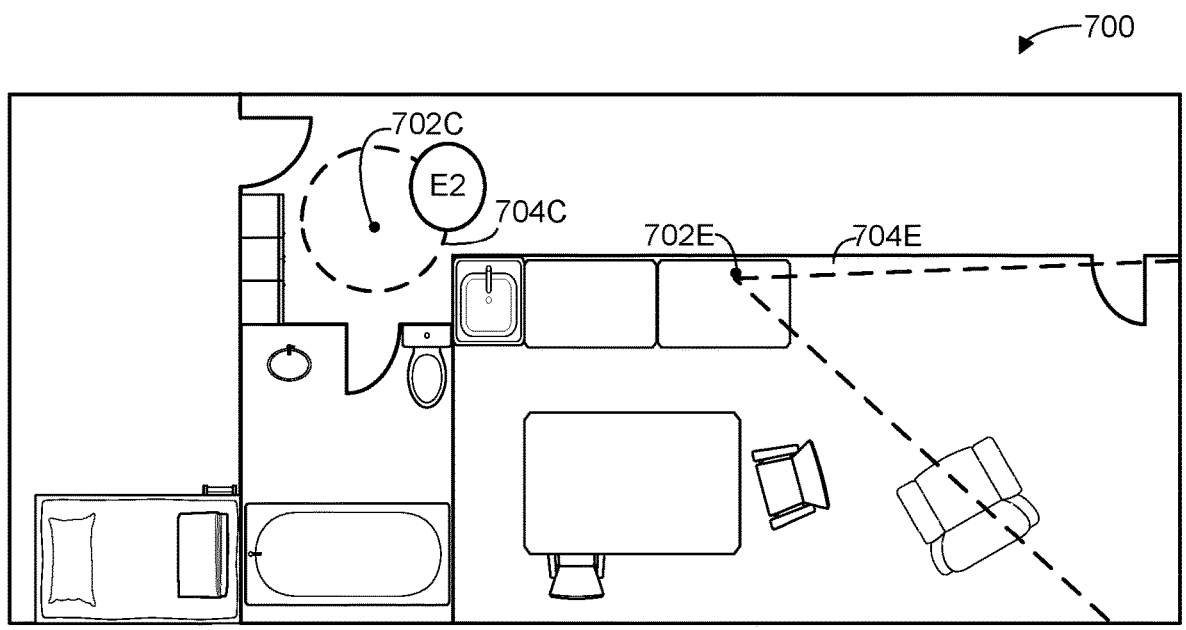

Accordingly, in FIG. 14D, the entity-tracking computing device has determined that the environment-relative position of the second entity is consistent with the environment-relative position of the first entity, and therefore concluded that the first and second entities are the same. Accordingly, as discussed above, a unique entity identifier previously assigned to the first entity may be assigned to the second entity. As shown in FIG. 14D, the entity tracking-computing device is able to conclude that only second entity E2 is present in environment 700.

It will be understood that, in some cases, additional or alternative considerations may be taken into account when determining that the environment-relative position of one entity is consistent with the environment-relative position of another entity. For example, in some cases, determining that the environment-relative position of the second entity is consistent with the environment-relative position of the first entity includes determining that one or more identifying characteristics of the second entity are within a threshold similarity of one or more identifying characteristics of the first entity. In other words, upon detecting an entity, a sensor and/or entity-tracking computing device may quantify an appearance of the entity based on one or more identifying characteristics, which can include, for example, the entity's size, shape, gait, facial features, voice, and/or other identifying criteria discussed above. Such identifying characteristics may, for example, be used to construct a multi-dimensional feature vector for the entity. Upon detecting an entity, the relative similarity of the two entities may be quantified by comparing the identifying characteristics of the two entities. If the two entities have highly similar identifying characteristics, it may be determined that the two entities are in fact the same.

With reference now to FIGS. 15-17, additional example implementations of smart assistant device 20 in a single computing device and across multiple computing devices are illustrated. Additional details regarding components and computing aspects of computing devices illustrated in FIGS. 15-17 are described below with reference to FIG. 18.

FIG. 15 shows an example of an all-in-one computing device 160 in which the components implementing smart assistant device 20 are arranged together in a standalone device. In some examples, all-in-one computing device 160 may be communicatively coupled to one or more other computing devices 162 via a network 166. In some examples, all-in-one computing device 160 may be communicatively coupled to a data store 164 that may store a variety of data, such as user profile data. All-in-one computing device 160 includes at least one sensor 22, voice listener 30, parser 40, intent handler 50, commitment engine 60, entity-tracking computing system 100, and at least one output device 70. Sensor(s) 22 include at least one microphone to receive natural language inputs from a user. In some examples one or more other types of sensor(s) 22 also may be included.

As described above, voice listener 30, parser 40, and intent handler 50 work in concert to convert natural language inputs into commitments that are executable by the all-in-one device 160. Such commitments may be stored by commitment engine 60. The entity-tracking computing system 100 may provide context information to the commitment engine 60 and/or other modules. At a contextually appropriate time, the commitment engine 60 may execute a commitment and provide output, such as audio signals, to output device(s) 70.

FIG. 16 shows an example implementation in which one or more remote services 170 perform the natural language processing functionality of smart assistant device 20. In this example, voice listener 30, parser 40, intent handler 50, entity-tracking computing system 100 and commitment engine 60 reside on one or more computing devices, such as one or more servers, that are remotely located from a cloud-supported user device A. Sensor data from one or more sensors 22 of the user device A is provided to remote service(s) 170 via a network. For example, audio data of a user speaking may be captured by a microphone of user device A and provided to voice listener 30.

As described above, voice listener 30, parser 40, and intent handler 50 cooperate to convert the audio data into commitments that are stored in commitment engine 60. At a contextually appropriate time, the commitment engine 60 may execute a commitment and provide output, such as audio signals, to one or more output device(s) 70 of the user device A.

FIG. 17 shows another example implementation in which one or more remote services 170 perform the natural language processing functionality of smart assistant device 20. In this example, the one or more remote services 170 are communicatively coupled with a plurality of different sensors 22 and output devices 70. In this example, the sensors include individual standalone sensors A and C, such as microphones, cameras, etc. The output devices include individual standalone output devices B and D, such as loudspeakers.

The one or more remote services 170 are also communicatively coupled to a device E that includes one or more sensors F and an output device G. Device E may take the form of a simple standalone device comprising a microphone, speaker and network connectivity components. In other examples, device E may be a mobile phone, tablet computer, wall-mounted display, or other suitable computing device. In some examples, device E, sensors A and C, and output devices B and D may be part of the same cloud-supported client. In other examples, any number of individual sensors and devices may be utilized with the one or more remote services 170.

As described above, the one or more remote services 170 perform the natural language processing functionality of smart assistant device 20. In some examples, one or more of the remote services 170 may include all of the natural language processing modules of smart assistant device 20, as shown in the example of FIG. 10. In other examples, one or more remote services 170 may include less than all of the natural language processing modules, and may be communicatively coupled to the other modules located at one or more other service(s). In the present example, one or more of the remote services 170 also may comprise a device selector 174 that may utilize sensor inputs to select output device B, D and/or G to receive output from the commitment engine 60.

In some embodiments, the methods and processes described herein may be tied to a computing system of one or more computing devices. In particular, such methods and processes may be implemented as a computer-application program or service, an application-programming interface (API), a library, and/or other computer-program product.

Figure 18:
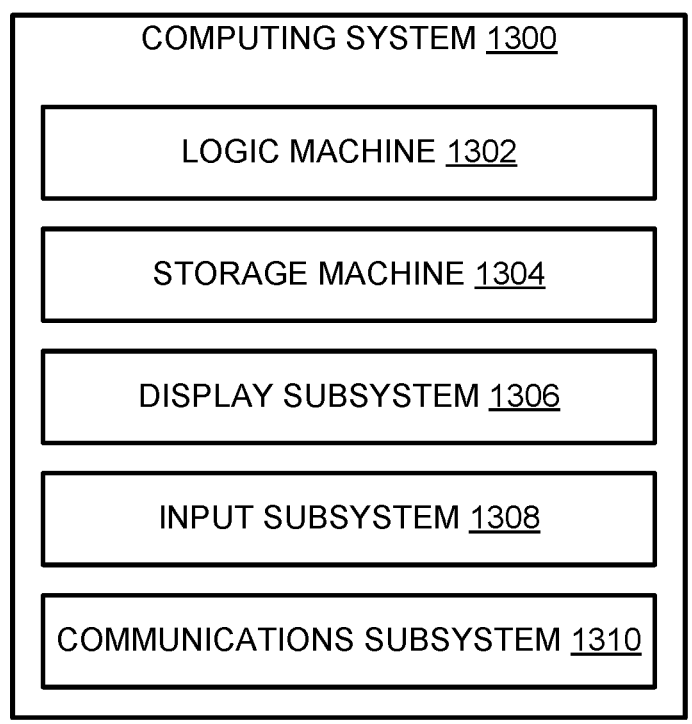
FIG. 18 schematically shows a computing system according to examples of the present disclosure.

FIG. 18 schematically shows a non-limiting embodiment of a computing system 1300 that can enact one or more of the methods and processes described above. Computing system 1300 is shown in simplified form. Computing system 1300 may take the form of one or more personal computers, server computers, tablet computers, home-entertainment computers, network computing devices, gaming devices, mobile computing devices, mobile communication devices (e.g., smart phone), and/or other computing devices.

Computing system 1300 includes a logic machine 1302 and a storage machine 1304. Computing system 1300 may optionally include a display subsystem 1306, input subsystem 1308, communication subsystem 1310, and/or other components not shown in FIG. 18.

Logic machine 1302 includes one or more physical devices configured to execute instructions. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic machine may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of the logic machine optionally may be distributed among two or more separate devices, which may be remotely located and/or configured for coordinated processing. Aspects of the logic machine may be virtualized and executed by remotely accessible, networked computing devices configured in a cloud-computing configuration.

Storage machine 1304 includes one or more physical devices configured to hold instructions executable by the logic machine to implement the methods and processes described herein. When such methods and processes are implemented, the state of storage machine 1304 may be transformed—e.g., to hold different data.

Storage machine 1304 may include removable and/or built-in devices. Storage machine 1304 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage machine 1304 may include volatile, nonvolatile, dynamic, static, read/write, read-only, random-access, sequential-access, location-addressable, file-addressable, and/or content-addressable devices.

It will be appreciated that storage machine 1304 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 1302 and storage machine 1304 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 1300 implemented to perform a particular function. In some cases, a module, program, or engine may be instantiated via logic machine 1302 executing instructions held by storage machine 1304. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

It will be appreciated that a "service", as used herein, is an application program executable across multiple user sessions. A service may be available to one or more system components, programs, and/or other services. In some implementations, a service may run on one or more server-computing devices.

When included, display subsystem 1306 may be used to present a visual representation of data held by storage machine 1304. This visual representation may take the form of a graphical user interface (GUI). As the herein described methods and processes change the data held by the storage machine, and thus transform the state of the storage machine, the state of display subsystem 1306 may likewise be transformed to visually represent changes in the underlying data. Display subsystem 1306 may include one or more display devices utilizing virtually any type of technology. Such display devices may be combined with logic machine 1302 and/or storage machine 304 in a shared enclosure, or such display devices may be peripheral display devices.

When included, input subsystem 1308 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 1310 may be configured to communicatively couple computing system 1300 with one or more other computing devices. Communication subsystem 1310 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 1300 to send and/or receive messages to and/or from other devices via a network such as the Internet.

In an example, an entity-tracking computing system comprises: a logic machine; a communication subsystem; and a storage machine holding instructions executable by the logic machine to: via the communication subsystem, communicatively couple the entity-tracking computing system to a plurality of sensors each having a field-of-detection (FOD) within an environment; maintain an environment-relative coordinate system to which the FOD of each sensor of the plurality of sensors is mapped; receive, via the communication subsystem and from a first sensor of the plurality of sensors, an indication of presence of a first entity within a FOD of the first sensor at a sensor-relative position within a sensor-relative coordinate system of the first sensor; translate the sensor-relative position of the first entity to an environment-relative position of the first entity within the environment-relative coordinate system; assign a unique entity identifier to the first entity; receive, from a second sensor of the plurality of sensors, an indication of presence of a second entity within a FOD of the second sensor at a sensor-relative position within a sensor-relative coordinate system of the second sensor; translate the sensor-relative position of the second entity to an environment-relative position of the second entity within the environment-relative coordinate system; and based on determining that the environment-relative position of the second entity is consistent with the environment-relative position of the first entity, assign the unique entity identifier to the second entity. In this example or any other example, mapping the FOD of a sensor of the plurality of sensors to the environment-relative coordinate system includes resolving a position of a calibration device relative to the sensor, and identifying a correspondence between the position of the calibration device and the FOD of the sensor. In this example or any other example, resolving the position of the calibration device includes receiving from the calibration device information useable to assess the position of the calibration device within the environment-relative coordinate system. In this example or any other example, the sensor incorporates a positioning marker, and the instructions are further executable to receive, from the calibration device, information useable to assess a position of the positioning marker within the environment-relative coordinate system. In this example or any other example, the calibration device incorporates a positioning marker, and the instructions are further executable to receive, from the sensor, information useable to assess a position of the positioning marker within a sensor-relative coordinate system of the sensor. In this example or any other example, the first entity is unidentified, and the unique entity identifier is a generic identifier. In this example or any other example, data received from the second sensor is useable to identify the second entity as a previously-identified human, and the instructions are further executable to replace the generic identifier with a previously-assigned entity identifier associated with the previously-identified human. In this example or any other example, the first entity is previously-identified human, and the unique entity identifier is a previously-assigned entity identifier associated with the previously-identified human. In this example or any other example, the first sensor is a camera, and the data received from the camera includes information usable to identify a human face in the first FOD. In this example or any other example, data received from the second sensor is not sufficient to identify the second entity without the data received from the first sensor. In this example or any other example, determining that the environment-relative position of the second entity is consistent with the environment-relative position of the first entity includes determining that the environment-relative position of the second entity is within a threshold distance of the environment-relative position of the first entity according to the environment-relative coordinate system. In this example or any other example, the instructions are further executable to predict a path of the first entity after the first entity leaves the FOD of the first sensor, and determining that the environment-relative position of the second entity is consistent with the environment-relative position of the first entity includes determining that the environment-relative position of the second entity is consistent with the path after the second entity enters the FOD of the second sensor. In this example or any other example, determining that the environment-relative position of the second entity is consistent with the environment-relative position of the first entity includes determining that one or more identifying characteristics of the second entity are within a threshold similarity of one or more identifying characteristics of the first entity. In this example or any other example, the plurality of sensors includes a plurality of cameras. In this example or any other example, the plurality of cameras includes one or more infrared (IR) cameras. In this example or any other example, the plurality of cameras includes one or more depth cameras. In this example or any other example, the plurality of cameras includes one or more downward-facing overhead cameras. In this example or any other example, the plurality of sensors includes a radar sensor.

In an example, a method for tracking entities in an environment comprises: maintaining an environment-relative coordinate system to which a field-of-detection (FOD) of each of a plurality of sensors is mapped, each of the plurality of sensors having a FOD within the environment;

receiving an indication of presence of a first entity within a FOD of a first sensor of the plurality of sensors at a sensor-relative position within a sensor-relative coordinate system of the first sensor; translating the sensor-relative position of the first entity to an environment-relative position of the first entity within the environment-relative coordinate system; assigning a unique entity identifier to the first entity; receiving an indication of presence of a second entity within a FOD of a second sensor of the plurality of sensors at a sensor-relative position within a sensor-relative coordinate system of the second sensor; translating the sensor-relative position of the second entity to an environment-relative position of the second entity within the environment-relative coordinate system; and based on determining that the environment-relative position of the second entity is consistent with the environment-relative position of the first entity, assigning the unique entity identifier to the second entity.

In an example, an entity-tracking computing system comprises; a logic machine; a communication subsystem; and a storage machine holding instructions executable by the logic machine to: via the communication subsystem, communicatively couple the entity-tracking computing system to a plurality of sensors each having a field-of-detection (FOD) within an environment, the plurality of sensors including at least an infrared (IR) camera and a radar sensor; maintain an environment-relative coordinate system to which the FOD of each sensor of the plurality of sensors is mapped; receive, via the communication subsystem and from the IR camera, an indication of presence of a first entity within a FOD of the IR camera at a sensor-relative position within a sensor-relative coordinate system of the IR camera; translate the sensor-relative position of the first entity to an environment-relative position of the first entity within the environment-relative coordinate system; identify the first entity as a previously-identified human, and assign a unique entity identifier to the first entity, the unique entity identifier being a previously-assigned entity identifier associated with the previously-identified human; receive, from the radar sensor, an indication of presence of a second entity within a FOD of the radar sensor at a sensor-relative position within a sensor-relative coordinate system of the radar sensor; translate the sensor-relative position of the second entity to an environment-relative position of the second entity within the environment-relative coordinate system; and based on determining that the environment-relative position of the second entity is consistent with the environment-relative position of the first entity, assign the unique entity identifier to the second entity.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. An entity-tracking computing system, comprising:
a logic machine;
a communication subsystem; and
a storage machine holding instructions executable by the logic machine to:
via the communication subsystem, communicatively couple the entity-tracking computing system to a plurality of sensors each having a field-of-detection (FOD) within an environment;
maintain an environment-relative coordinate system to which the FOD of each sensor of the plurality of sensors is mapped, where mapping the FOD of a particular sensor of the plurality of sensors to the environment-relative coordinate system includes resolving a position of a calibration device relative to the particular sensor, and identifying a correspondence between the position of the calibration device and the FOD of the particular sensor;
receive, via the communication subsystem and from a first sensor of the plurality of sensors, an indication of presence of a first entity within a FOD of the first sensor at a sensor-relative position within a sensor-relative coordinate system of the first sensor;
translate the sensor-relative position of the first entity to an environment-relative position of the first entity within the environment-relative coordinate system;
assign a unique entity identifier to the first entity;
receive, from a second sensor of the plurality of sensors, an indication of presence of a second entity within a FOD of the second sensor at a sensor-relative position within a sensor-relative coordinate system of the second sensor;
translate the sensor-relative position of the second entity to an environment-relative position of the second entity within the environment-relative coordinate system; and
based on determining that the environment-relative position of the second entity is consistent with the environment-relative position of the first entity, assign the unique entity identifier to the second entity.

2. The entity-tracking computing system of claim 1, where resolving the position of the calibration device includes receiving from the calibration device information useable to assess the position of the calibration device within the environment-relative coordinate system.

3. The entity-tracking computing system of claim 2, where the particular sensor incorporates a positioning marker, and the instructions are further executable to receive, from the calibration device, information useable to assess a position of the positioning marker within the environment-relative coordinate system.

4. The entity-tracking computing system of claim 2, where the calibration device incorporates a positioning marker, and the instructions are further executable to receive, from the particular sensor, information useable to assess a position of the positioning marker within a sensor-relative coordinate system of the particular sensor.

5. The entity-tracking computing system of claim 1, where the first entity is unidentified, and where the unique entity identifier is a generic identifier.

6. The entity-tracking computing system of claim 5, where data received from the second sensor is useable to identify the second entity as a previously-identified human, and the instructions are further executable to replace the generic identifier with a previously-assigned entity identifier associated with the previously-identified human.

7. The entity-tracking computing system of claim 1, where the first entity is previously-identified human, and where the unique entity identifier is a previously-assigned entity identifier associated with the previously-identified human.

8. The entity-tracking computing system of claim 1, where the first sensor is a camera, and where the data received from the camera includes information usable to identify a human face in the first FOD.

9. The entity-tracking computing system of claim 1, where data received from the second sensor is not sufficient to identify the second entity without the data received from the first sensor.

10. The entity-tracking computing system of claim 1, where determining that the environment-relative position of the second entity is consistent with the environment-relative position of the first entity includes determining that the environment-relative position of the second entity is within a threshold distance of the environment-relative position of the first entity according to the environment-relative coordinate system.

11. The entity-tracking computing system of claim 1, where the instructions are further executable to predict a path of the first entity after the first entity leaves the FOD of the first sensor, and determining that the environment-relative position of the second entity is consistent with the environment-relative position of the first entity includes determining that the environment-relative position of the second entity is consistent with the path after the second entity enters the FOD of the second sensor.

12. The entity-tracking computing system of claim 1, where determining that the environment-relative position of the second entity is consistent with the environment-relative position of the first entity includes determining that one or more identifying characteristics of the second entity are within a threshold similarity of one or more identifying characteristics of the first entity.

13. The entity-tracking computing system of claim 1, where the plurality of sensors includes a plurality of cameras.

14. The entity-tracking computing system of claim 13, where the plurality of cameras includes one or more infrared (IR) cameras.

15. The entity-tracking computing system of claim 13, where the plurality of cameras includes one or more depth cameras.

16. The entity-tracking computing system of claim 13, where the plurality of cameras includes one or more downward-facing overhead cameras.

17. The entity-tracking computing system of claim 1, where the plurality of sensors includes a radar sensor.

18. A method for tracking entities in an environment, comprising:
  maintaining an environment-relative coordinate system to which a field-of-detection (FOD) of each of a plurality of sensors is mapped, each of the plurality of sensors having a FOD within the environment, where mapping the FOD of a particular sensor of the plurality of sensors to the environment-relative coordinate system includes resolving a position of a calibration device relative to the particular sensor, and identifying a correspondence between the position of the calibration device and the FOD of the particular sensor;
  receiving an indication of presence of a first entity within a FOD of a first sensor of the plurality of sensors at a sensor-relative position within a sensor-relative coordinate system of the first sensor;
  translating the sensor-relative position of the first entity to an environment-relative position of the first entity within the environment-relative coordinate system;
  assigning a unique entity identifier to the first entity;
  receiving an indication of presence of a second entity within a FOD of a second sensor of the plurality of sensors at a sensor-relative position within a sensor-relative coordinate system of the second sensor;
  translating the sensor-relative position of the second entity to an environment-relative position of the second entity within the environment-relative coordinate system; and
  based on determining that the environment-relative position of the second entity is consistent with the environment-relative position of the first entity, assigning the unique entity identifier to the second entity.

19. An entity-tracking computing system, comprising:
  a logic machine;
  a communication subsystem; and
  a storage machine holding instructions executable by the logic machine to:
    via the communication subsystem, communicatively couple the entity-tracking computing system to a plurality of sensors each having a field-of-detection (FOD) within an environment, the plurality of sensors including at least an infrared (IR) camera and a radar sensor;
    maintain an environment-relative coordinate system to which the FOD of each sensor of the plurality of sensors is mapped;
    receive, via the communication subsystem and from the IR camera, an indication of presence of a first entity within a FOD of the IR camera at a sensor-relative position within a sensor-relative coordinate system of the IR camera;
    translate the sensor-relative position of the first entity to an environment-relative position of the first entity within the environment-relative coordinate system;
    identify the first entity as a previously-identified human, and assign a unique entity identifier to the first entity, the unique entity identifier being a previously-assigned entity identifier associated with the previously-identified human;
    receive, from the radar sensor, an indication of presence of a second entity within a FOD of the radar sensor at a sensor-relative position within a sensor-relative coordinate system of the radar sensor;
    translate the sensor-relative position of the second entity to an environment-relative position of the second entity within the environment-relative coordinate system; and
    based on determining that the environment-relative position of the second entity is consistent with the environment-relative position of the first entity, assign the unique entity identifier to the second entity.

* * * * *